United States Patent
Duerfeldt et al.

(10) Patent No.: US 11,447,452 B2
(45) Date of Patent: Sep. 20, 2022

(54) AGONISTS OF PEROXISOME PROLIFERATOR-ACTIVATED RECEPTOR ALPHA AND METHODS OF USE

(71) Applicant: The Board of Regents of the University of Oklahoma, Norman, OK (US)

(72) Inventors: Adam Duerfeldt, Norman, OK (US); Jian-xing Ma, Edmond, OK (US); Xiaozheng Dou, Norman, OK (US); Dinesh Nath, Meerut (IN); Young-Hwa Shin, Oklahoma City, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 0 days.

(21) Appl. No.: 16/981,483

(22) PCT Filed: Mar. 15, 2019

(86) PCT No.: PCT/US2019/022400
§ 371 (c)(1),
(2) Date: Sep. 16, 2020

(87) PCT Pub. No.: WO2019/178439
PCT Pub. Date: Sep. 19, 2019

(65) Prior Publication Data
US 2021/0024469 A1 Jan. 28, 2021

Related U.S. Application Data

(60) Provisional application No. 62/643,998, filed on Mar. 16, 2018.

(51) Int. Cl.
*C07D 215/52* (2006.01)
*C07C 69/734* (2006.01)
*C07D 263/32* (2006.01)
*C07D 277/56* (2006.01)

(52) U.S. Cl.
CPC .......... *C07D 215/52* (2013.01); *C07C 69/734* (2013.01); *C07D 263/32* (2013.01); *C07D 277/56* (2013.01)

(58) Field of Classification Search
CPC .. C07C 69/734; C07D 263/32; C07D 277/56; C07D 215/52
See application file for complete search history.

(56) References Cited

U.S. PATENT DOCUMENTS 9,199,980 B2 12/2015 Armani et al.
2006/0069013 A1 3/2006 Ostergaard et al.
2008/0200535 A1 8/2008 Ohmori et al.

OTHER PUBLICATIONS

Dou, Bioorg & Med Chem Lett, vol. 28, 2018, 2717-2722. (Year: 2018).*
Link, Bioorg & Med Chem Lett, vol. 14, 2004, 4169-4172. (Year: 2004).*
Brauer, J Comb Chem, vol. 7, 2005, 218-226. (Year: 2005).*
Link, J Med CHem, vol. 48, 2005, 5295-5304. (Year: 2005).*
Yang, Chem Res Toxicol, vol. 23, 2010, 1691-1700. (Year: 2010).*
Korczynska, J Med Chem, vol. 59, 2016, 1580-1598. (Year: 2016).*
Zhang, J Ophthalmology, vol. 2015, Article ID 275435, 10 pages, 2015. (Year: 2015).*
PCT/US2019/022400; International Search Report and Written Opinion; International Searching Authority; dated Jul. 16, 2019; 15 pages.
International Application No. PCT/US2019/022400; "International Search Report and Written Opinion"; dated Jul. 16, 2019; 15 pages.

* cited by examiner

*Primary Examiner* — D Margaret M Seaman
(74) *Attorney, Agent, or Firm* — Hall Estill Law Firm

(57) ABSTRACT

Benzyl derivative compounds having peroxisome proliferator-activated receptor α (PPARα) agonistic activity, compositions containing such compounds, and methods of their use in enhancing PPARα activity for treating diseases and/or conditions involving inflammation and/or angiogenesis, particularly ocular diseases and/or conditions such as but not limited to retinal inflammation, retinal neovascularization, retinal vascular leakage, retinopathy of prematurity, diabetic retinopathy, age-related macular degeneration, and diabetic macular edema are disclosed.

13 Claims, 8 Drawing Sheets

AGONISTS OF PEROXISOME PROLIFERATOR-ACTIVATED RECEPTOR ALPHA AND METHODS OF USE

CROSS-REFERENCE TO RELATED APPLICATIONS

The present application is a national stage application of a PCT application having International Application No. PCT/US2019/022400, filed Mar. 15, 2019, which claims priority to U.S. Provisional Application having U.S. Ser. No. 62/643,998, filed Mar. 16, 2018, which claims the benefit under 35 U.S.C. 119(e), the disclosure of which is hereby expressly incorporated herein by reference.

GOVERNMENT SUPPORT

This invention was made with government support under Grant Number R21EY028279 awarded by the National Eye Institute of the National Institutes of Health (NIH). The government has certain rights in the invention.

BACKGROUND

Retinal inflammation and resultant neovascularization (NV) are major causes of vision loss in a number of ocular disorders such as retinopathy of prematurity (ROP), diabetic retinopathy (DR) and age-related macular degeneration (AMD). Diabetic macular edema (DME) is caused by retinal vascular leakage and is the primary cause of vision loss in diabetic eye disease. Accumulating evidence suggests that DR is a chronic inflammatory disorder, as multiple inflammatory factors such as tumor necrosis factor-alpha (TNF-α), intercellular adhesion molecule-1 (ICAM-1), and vascular endothelial growth factor (VEGF) are over-expressed in the diabetic retina. Inflammation plays a causative role in impaired retinal vascular endothelial function, vascular leakage and later retinal NV. Anti-VEGF has emerged as a primary treatment option, but suffers from the requirement of frequent intraocular injections, high cost, and the need for specialized facilities. Additionally, although effective for most, ~40-50% of patients are refractory to intravitreal injection of anti-VEGF and corticosteroids. This implies that auxiliary pathways and factors that remain unaddressed with current interventions are involved in disease causation and progression.

The peroxisome proliferator-activated receptors (PPARs) are a family of nuclear hormone-activated receptors and transcription factors. The PPAR family includes three members, PPAR alpha (PPARα), PPAR gamma (PPARγ), and PPAR delta (PPARδ), the latter of which is sometimes referred to in the art as PPAR beta (PPARβ). Although these three PPAR members share significant sequence homology, they have different tissue distributions, diverse functions, and can be selectively targeted. While PPARγ is primarily expressed in adipose tissue, PPARα is expressed in cells with high mitochondrial activities including the liver, vascular endothelial cells (ECs), smooth muscle cells, kidney and heart. Preliminary studies have shown that PPARα is abundantly expressed in the retina. Only recently, however, have the roles of PPARα in regulating inflammation, apoptosis, and neovascularization (NV) in diabetic retinas been revealed, establishing a new avenue for PPARα agonists as therapeutics for oculovascular diseases. Upon activation by endogenous or exogenous synthetic agonists, PPARα forms a heterodimer with retinoid x receptor (RXR) and binds to the PPAR responsive element (PPRE) in the promoter of its target genes activating target gene transcription. In addition, PPARα indirectly regulates other genes by interfering with their transcriptional regulation. PPARα has been shown to regulate a large number of genes involved in lipid metabolism and vascular inflammation such as nuclear factor kappa-light-chain-enhancer of activated B cells (NF-κB), ICAM-1 and interleukin-6 (IL-6). Furthermore, PPARα has been shown to regulate oxidation and angiogenesis. However, the function of PPARα in the retina is poorly understood. The role of PPARα in DR was unrecognized until findings from the FIELD and ACCORD clinical trials demonstrated that the PPARα agonist fenofibric acid (a metabolite of fenofibrate) had a robust and unanticipated therapeutic effect on DR, reducing the need for laser treatment by 32-40% in type 2 diabetic patients. Previous studies have demonstrated that PPAR levels are decreased in the retinas of both type 1 and type 2 diabetic animal models. Furthermore, activation of PPARα by fenofibrate effectively reduced retinal leukostasis and vascular leakage in diabetic models and ameliorates ischemia-induced retinal NV.

Fenofibrate was originally recognized for its ability to lower cholesterol and triglyceride levels and has thus been widely used clinically for the treatment of hyperlipidemia for more than 30 years. Fenofibrate is the first low-cost and safe oral drug for DR with clinically proven efficacy against NV and DME in DR patients and is thus of great interest to clinicians, basic scientists and pharmaceutical companies interested in the development of novel DR therapeutics. It has been reported that the protective effects of fenofibrate on retinal NV and DME are not correlated with its lipid-lowering activity, but rather arise from interaction of its metabolite, fenofibric acid, with PPARα. Fenofibrate thus has significant therapeutic potential in the treatment of DR and AMD, but has a relatively low binding affinity for PPARα, and has off-target nephrotoxic effects and other potential side effects. A critical need exists to develop new treatment options that are non-invasive and complementary to current approaches. Development of higher affinity agonists of PPARα to further improve the treatment for DR and other inflammatory and angiogenic disorders of the eye and elsewhere in the body is desirable and is the goal to which the present work is directed.

DETAILED DESCRIPTION

Figure 1:
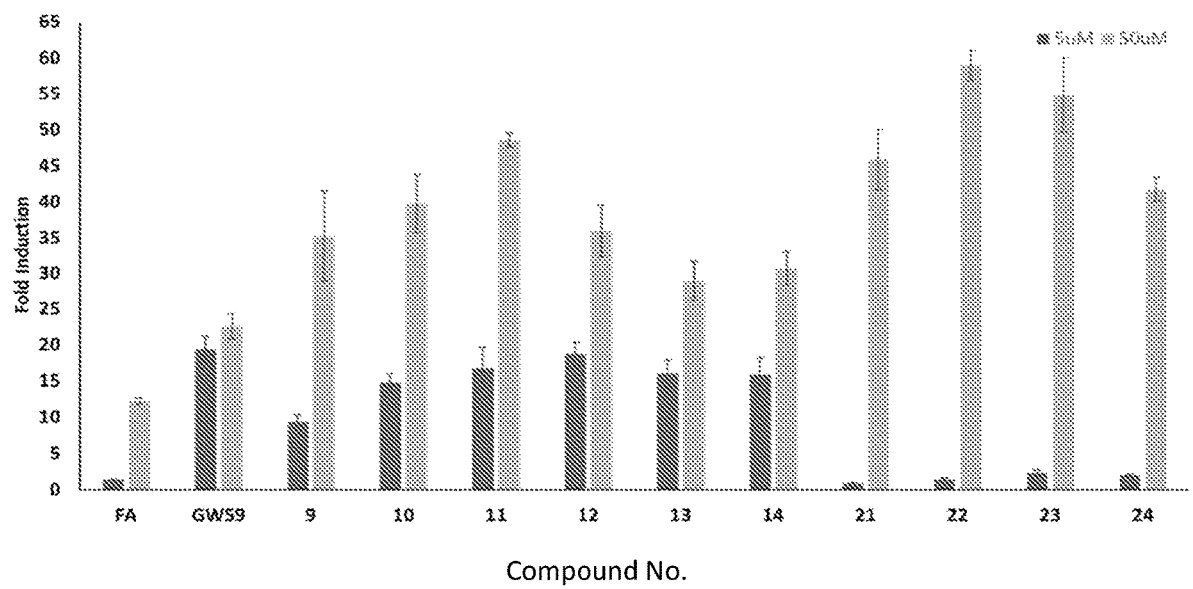
FIG. 1 shows initial evaluation results of compounds 9-14 and 21-24 for hPPARα agonism in a cell-based luciferase assay. Results are presented from a single experiment as fold-induction versus the DMSO control±S.E. (n=3). Compound GW590735 was evaluated at 5 μM and 10 μM.

As noted above, retinal inflammation and neovascularization are major causes of vision loss in a number of ocular disorders such as retinopathy of prematurity, diabetic retinopathy (DR), and age-related macular degeneration (AMD). Two large, prospective clinical studies reported that fenofibrate, an agonist of PPARα, has robust therapeutic effects in DR. Disclosed herein is a new class of compounds which, due to PPAR agonistic activity, have an effect on retinal endothelial dysfunction, angiogenesis and inflammation, indicating a therapeutic effect in, for example, DR and AMD (e.g., wet AMD). The compositions of the present disclosure may be used in treatments for ocular disorder or conditions such as, but not limited to, DR, AMD (e.g., wet AMD), retinal inflammation, retinal neovascularization (NV), retinal vascular leakage, retinopathy of prematurity (ROP), and diabetic macular edema (DME). Other diseases and/or conditions associated with inflammation and/or angiogenesis which can be treated using the compounds of the present disclosure are described below.

Before further describing various embodiments of the compounds, compositions and methods of the present disclosure in more detail by way of exemplary description, examples, and results, it is to be understood that the compounds, compositions, and methods of present disclosure are not limited in application to the details of specific embodiments and examples as set forth in the following description. The description provided herein is intended for purposes of illustration only and is not intended to be construed in a limiting sense. As such, the language used herein is intended to be given the broadest possible scope and meaning; and the embodiments and examples are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the present disclosure. However, it will be apparent to a person having ordinary skill in the art that the present disclosure may be practiced without these specific details. In other instances, features which are well known to persons of ordinary skill in the art have not been described in detail to avoid unnecessary complication of the description. It is intended that all alternatives, substitutions, modifications and equivalents apparent to those having ordinary skill in the art are included within the scope of the present disclosure. All of the compounds, compositions, and methods of production and application and use thereof disclosed herein can be made and executed in light of the present disclosure. Thus, while the compounds, compositions, and methods of the present disclosure have been described in terms of particular embodiments, it will be apparent to those of skill in the art that variations may be applied to the compounds, compositions and/or methods and in the steps or in the sequence of steps of the methods described herein without departing from the concept, spirit, and scope of the inventive concepts described herein.

All patents, published patent applications, and non-patent publications mentioned in the specification or referenced in any portion of this application are herein expressly incorporated by reference in their entirety to the same extent as if each individual patent or publication was specifically and individually indicated to be incorporated by reference.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular.

As utilized in accordance with the methods and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth. Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, includes ranges of 1-20, 10-50, 50-100, 100-500, and 500-1,000, for example.

As used in this specification and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the terms "about" and "approximately" are used to indicate that a value includes the inherent variation of error for the composition, the method used to administer the composition, or the variation that exists among the study subjects. As used herein the qualifiers "about" or "approximately" are intended to include not only the exact value, amount, degree, orientation, or other qualified characteristic or value, but are intended to include some slight variations due to measuring error, manufacturing tolerances, stress exerted on various parts or components, observer error, wear and tear, and combinations thereof, for example. The term "about" or "approximately", where used herein when referring to a measurable value such as an amount, a temporal duration, and the like, is meant to encompass, for example, variations of ±20%, or ±15%, or ±10%, or ±5%, or ±1%, or ±0.1% from the specified value, as such variations are appropriate to perform the disclosed methods and as understood by persons having ordinary skill in the art. As used herein, the term "substantially" means that the subsequently described event or circumstance completely occurs or that the subsequently described event or circumstance occurs to a great extent or degree. For example, the term "substantially" means that the subsequently described event or circumstance occurs at least 75% of the time, or at least 80% of the time, or at least 90% of the time, or at least 95% of the time, or at least 98% of the time.

As used herein any reference to "one embodiment" or "an embodiment" means that a particular element, feature, structure, or characteristic described in connection with the embodiment is included in at least one embodiment and may be included in other embodiments. The appearances of the phrase "in one embodiment" in various places in the specification are not necessarily all referring to the same embodiment and are not necessarily limited to a single or particular embodiment.

The term "pharmaceutically acceptable" refers to compounds and compositions which are suitable for administration to humans and/or animals without undue adverse side effects such as toxicity, irritation and/or allergic response commensurate with a reasonable benefit/risk ratio. The compounds of the present disclosure may be combined with one or more pharmaceutically-acceptable excipients, including carriers, vehicles, diluents, and adjuvents which may improve solubility, deliverability, dispersion, stability, and/or conformational integrity of the compounds or conjugates thereof.

As used herein, "pure," or "substantially pure" means an object species is the predominant species present (i.e., on a molar basis it is more abundant than any other object species in the composition thereof), and particularly a substantially purified fraction is a composition wherein the object species comprises at least about 50 percent (on a molar basis) of all macromolecular species present. Generally, a substantially pure composition will comprise more than about 80% of all macromolecular species present in the composition, more particularly more than about 85%, more than about 90%, more than about 95%, or more than about 99%. The term "pure" or "substantially pure" also refers to preparations where the object species is at least 60% (w/w) pure, or at least 70% (w/w) pure, or at least 75% (w/w) pure, or at least 80% (w/w) pure, or at least 85% (w/w) pure, or at least 90% (w/w) pure, or at least 92% (w/w) pure, or at least 95% (w/w) pure, or at least 96% (w/w) pure, or at least 97% (w/w) pure, or at least 98% (w/w) pure, or at least 99% (w/w) pure, or 100% (w/w) pure.

Non-limiting examples of animals or mammals within the scope and meaning of this term include dogs, cats, rats, mice, rabbits, guinea pigs, chinchillas, horses, goats, pigs, cattle, sheep, zoo animals, Old and New World monkeys, non-human primates, and humans.

In at least certain embodiments, the disease and/or condition which can be treated with a compound of the present disclosure is characterized by inflammation and/or angiogenesis. Such diseases and/or conditions having an inflammatory basis which can be treated with a compound of the present disclosure, include, but are not limited to, inflammatory bowel disease, type 1 or 2 diabetes, Graves disease, multiple sclerosis, various types of arthritis, vasculitis, dermatitis, glomerulonephritis, hepatitis, periodonititis, atherosclerosis, heart failure, obesity, Alzheimer's disease, and metabolic syndrome, and other disorders and conditions disclosed herein.

Examples of ocular diseases having an inflammatory basis which can be treated with a compound of the present disclosure, include, but are not limited to, keratitis, endophthalmitis, blepharitis, conjunctivitis, scleritis, herpetic inflammation, uveitis, vasculitis, arteritis, orbital inflammations, optic neuritis, sympathetic ophthalmia, retinitis, and other autoimmune diseases, age-related macular degeneration, macular edema, diabetic retinopathy, glaucoma, proliferative vitreoretinopathy, corneal edema, uveal edema, and retinal edema.

Diseases and/or conditions having an angiogenic basis which can be treated with a compound of the present disclosure, include, ocular diseases and/or conditions such as, but not limited to, diabetic retinopathy, age-related macular degeneration, retinopathy of prematurity, retinal artery or vein occlusion, corneal graft rejection, corneal neovascularization, neovascular glaucoma and sickle cell retinopathy, and non-ocular diseases and/or conditions including, but not limited to, cancer, skin diseases, diabetic ulcers, diabetic nephropathy, cardiovascular disease and stroke.

"Treatment" refers to therapeutic treatments. "Prevention" refers to prophylactic or preventative treatment measures or reducing the onset of a condition or disease. The term "treating" refers to administering the composition to a subject for therapeutic purposes and/or for prevention. Non-limiting examples of modes of administration include oral, topical, retrobulbar, subconjunctival, transdermal, parenteral, subcutaneous, intranasal, intramuscular, intraperitoneal, intravitreal, and intravenous routes, including both local and systemic applications. In addition, the compositions of the present disclosure may be formulated with carrier compounds which provide delayed, controlled, extended, and/or sustained release, for example using formulation techniques which incorporate the active agent into a degradable polymer.

The term "topical" is used herein to define a mode of administration through an epithelial surface, such as but not limited to, a material that is administered by being applied externally to the eye. A non-limiting example of topical administration is through the use of eyedrops, or application of active agent-containing particles.

The terms "therapeutic composition" and "pharmaceutical composition" refer to composition comprising a compound of the present disclosure (also referred to herein as an active agent) that may be administered to a subject by any method known in the art or otherwise contemplated herein, wherein administration of the composition brings about a therapeutic effect as described elsewhere herein. As noted, the compositions of the present disclosure may be designed to provide delayed, controlled, extended, and/or sustained release using appropriate formulation techniques.

The term "effective amount" refers to an amount of an active agent which is sufficient to exhibit a detectable therapeutic or treatment effect in a subject without excessive adverse side effects (such as substantial toxicity, irritation and allergic response) commensurate with a reasonable benefit/risk ratio when used in the manner of the present disclosure. The effective amount for a subject will depend upon the subject's type, size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein. The term "activity-enhancing amount" refers to an amount of an active agent which is sufficient to increase PPARα activity in a cell or subject.

The term "ameliorate" means a detectable or measurable improvement in a subject's condition or symptom thereof. A detectable or measurable improvement includes a subjective or objective decrease, reduction, inhibition, suppression, limit or control in the occurrence, frequency, severity, progression, or duration of the condition, or an improvement in a symptom or an underlying cause or a consequence of the condition, or a reversal of the condition. A successful treatment outcome can lead to a "therapeutic effect," or "benefit" of ameliorating, decreasing, reducing, inhibiting, suppressing, limiting, controlling or preventing the occurrence, frequency, severity, progression, or duration of a condition, or consequences of the condition in a subject.

A decrease or reduction in worsening, such as stabilizing the condition, is also a successful treatment outcome. A therapeutic benefit therefore need not be complete ablation or reversal of the condition, or any one, most or all adverse symptoms, complications, consequences or underlying causes associated with the condition. Thus, a satisfactory endpoint may be achieved when there is an incremental improvement such as a partial decrease, reduction, inhibition, suppression, limit, control or prevention in the occurrence, frequency, severity, progression, or duration, or inhibition or reversal of the condition (e.g., stabilizing), over a short or long duration of time (e.g., seconds, minutes, hours).

Where used herein the terms alkyl, haloalkyl, alkoxyl, haloalkoxyl, alkenyl, and alkynyl are generally intended to refer to branched or unbranched structures comprising 1, 2, 3, 4, 5, 6, 7, 8, 9, or 10 carbons, unless otherwise designated. Haloalkyl may refer to, for example, a 1, 2, 3, 4, 5, 6, 7, 8, 9, or 10 carbon haloalkyl having 1 to 3 halogen atoms. Haloalkoxyl may refer to, for example, a 1, 2, 3, 4, 5, 6, 7, 8, 9, or 10 carbon haloalkyl having 1 to 3 halogen atoms. A halogen may refer to chlorine (Cl), fluorine (F), bromine (Br), and/or iodine (I). Halogen may be abbreviated as "halo" herein.

In at least certain embodiments, the present disclosure includes active agent compositions and methods for treating ocular disorders and conditions, and particularly retinal conditions and disorders, which in certain non-limiting embodiments, include retinal inflammation, retinal neovascularization, retinal vascular leakage, retinopathy of prematurity (ROP), diabetic retinopathy (DR), age-related macular degeneration (e.g., wet AMD), and diabetic macular edema (DME) (or others disorders or conditions described elsewhere herein) using a compound having the chemical structure I:

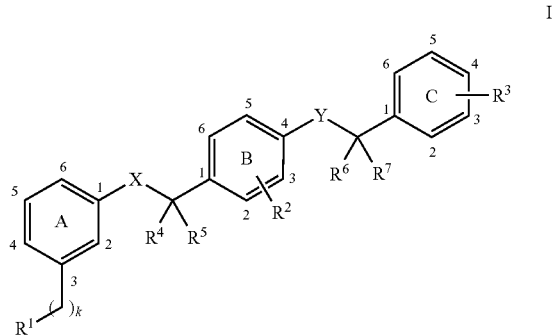

wherein ring A is a benzene, or a pyridine comprising nitrogen (N) in position 2, 4, 5, or 6;
wherein ring B is a benzene, or a pyridine comprising N in position 2, 3, 5, or 6;

wherein ring C is a benzene, or a pyridine comprising N in position 2, 3, 4, 5, or 6;

wherein X is selected from the group consisting of oxygen (O), NH, sulfur (S), and $CH_2$;

wherein Y is selected from the group consisting of O, NH, S, and $CH_2$;

wherein k is 0, 1, 2, 3, 4, 5, 6, 7, 8, 9, or 10 carbon atoms; and wherein in at least certain embodiments the $R^1$ substituent on the "A" ring of chemical structure I is selected from the chemical structures i-x shown in Table 1 below:

TABLE 1

Examples of $R^1$ substituents

| $R^1$ substituent no. | Chemical structure |
|---|---|
| i | carboxylic acid (–COOH) |
| ii | hydroxamic acid (–C(O)NHOH) |
| iii | N-hydroxy acetamide |
| iv | phosphonic acid (–P(O)(OH)$_2$) |
| v | phosphinic acid (–P(O)(H)(OH)) |
| vi | sulfonamide (–S(O)$_2$NH$_2$) |
| vii | acyl sulfonamide (–NHS(O)$_2$–) |
| viii | tetrazole |
| ix | –X–C(R$^8$)(R$^9$)–COOH |

TABLE 1-continued

Examples of $R^1$ substituents

| $R^1$ substituent no. | Chemical structure |
|---|---|
| x | –B(OR$^{10}$)(OR$^{11}$) |

In non-limiting embodiments, $R^8$ and $R^9$ of structure ix of Table 1 can be selected from the group: hydrogen (H), halogens (F, Cl, Br, I), alkyl (e.g., branched or unbranched, $C_1$ to $C_{10}$), alkoxy (e.g., branched or unbranched, $C_1$ to $C_{10}$), and cyclo ($R^8$ linked to $R^9$). In structure ix of Table 1, X can be O, NH, S, or $CH_2$. In non-limiting embodiments, $R^1$ and $R^{11}$ of structure x of Table 1 can be selected from the group: H, alkyl (e.g., branched or unbranched, $C_1$ to $C_{10}$), and cyclo ($R^{10}$ linked to $R^{11}$).

In other non-limiting examples, $R^1$ can be selected from the group: carboxylic acids, and carboxylic acid isosteres including hydroxamic acids, hydroxamic esters, phosphonic acids, phosphinic acids, sulfonic acids, sulfinic acids, sulfonamides, acyl sulfonamides, sulfonylureas, acylureas, tetrazoles, thiazolidine diones, oxazolidine diones, oxadiazol-5 (4H)-ones, thiadiazol-5(4H)-ones, oxathiadiazole-2-oxides, oxadiazol-5(4H)-thiones, isoxazoles, tetramic acids, cyclopentane 1,3-diones, cyclopentane 1,2-diones, squaric acids, substituted phenols, heteroarenes, amidines, hydroxyamides, alkyl hydroxyamidines, including the exemplary structures shown in Table 2, and further including salts of any of the above.

TABLE 2

Other examples of $R^1$

| Generic Group | Non-limiting examples, n = 0 – 4 |
|---|---|
| Carboxylic acids | –(CH$_2$)$_n$COOH |
| Hydroxamic acids | –(CH$_2$)$_n$C(O)NHOH ; –(CH$_2$)$_n$N(OH)C(O)– |
| Hydroxamic esters | –(CH$_2$)$_n$C(O)N(H)OMe ; –(CH$_2$)$_n$O–N(H)C(O)– |
| Phosphonic acids | –(CH$_2$)$_n$P(O)(OH)$_2$ |

TABLE 2-continued

Other examples of R¹

| Generic Group | Non-limiting examples, n = 0 – 4 |
|---|---|
| Phosphinic acids | (structure) |
| Sulfonic acids | (structure) |
| Sulfinic acids | (structure) |
| Sulfonamides | (structure) |
| Acyl sulfonamides | (structure) |
| Acyl sulfonamides | (structure) |
| Sulfonylureas | (structure) |
| Acylureas | (structure) |
| Tetrazoles | (structure) |
| Thiazolidine diones | (structure) |
| Oxazolidine diones | (structure) |
| Oxadiazol-5(4H)-ones | (structure) |
| Thiadiazol-5(4H)-ones | (structure) |
| Oxathiadiazole-2-oxides | (structure) |
| Oxadiazole-5(4H)-thiones | (structure) |
| Isoxazoles | (structure) |
| Tetramic acids | (structure) |
| Cyclopentane 1,3-diones | (structure) |
| Cyclopentane 1,2-diones | (structure) |
| Squaric acids | (structure) |

TABLE 2-continued

Other examples of $R^1$

| Generic Group | Non-limiting examples, n = 0 − 4 |
|---|---|
| | 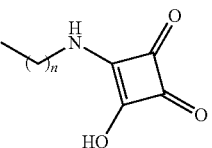 |
| Substituted phenols | 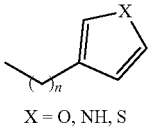 |
| Heteroarenes | 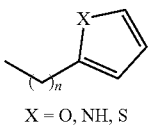<br>X = O, NH, S<br><br>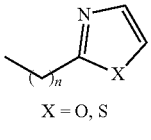<br>X = O, NH, S<br><br>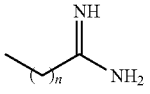<br>X = O, S |
| Amidines | 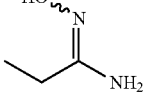 |

TABLE 2-continued

Other examples of $R^1$

| Generic Group | Non-limiting examples, n = 0 − 4 |
|---|---|
| Hydroxyamides | 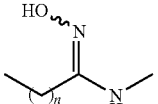 |
| Alkyl hydroxyamidines | |

In at least certain non-limiting embodiments, the $R^2$ substituent of chemical structure I is selected from the group: H, F, Cl, Br, I, nitro ($NO_2$), alkyl (e.g., $CH_3$, $CH_2CH_3$, or any alkyl chain with 3-10 carbon atoms, branched or unbranched), alkoxy (e.g., $OCH_3$, $OCH_2CH_3$, or any alkyoxy chain with 3-10 carbon atoms, branched or unbranched), haloalkyl (e.g., $CH_2Cl$, $CHBr_2$, $CF_3$), haloalkoxyl, (e.g., $OCH_2Cl$, $OCHBr_2$, $OCF_3$), a 1, 2, 3, 4, 5, 6, 7, 8, 9, or 10 carbon haloalkyl having e.g., 1 to 3 halogen atoms, a 1, 2, 3, 4, 5, 6, 7, 8, 9, or 10 carbon haloalkoxyl having, e.g., 1 to 3 halogen atoms, cycloalkyl, halocycloalkyl, O-para-alkylbenzyl (e.g., where alkyl is methyl, ethyl, or propyl); O-para-alkyloxybenzyl (e.g., where alkyl is methyl, ethyl, or propyl); and O-para-halobenzyl (wherein halo=Cl, F, Br, or I).

In at least certain non-limiting embodiments, the $R^3$ substituent of ring "C" of chemical structure I is selected from the group: H, F, Cl, Br, I, $NO_2$, alkyl (e.g., $CH_3$, $CH_2CH_3$, or any alkyl chain with 3-10 carbon atoms, branched or unbranched), alkoxy (e.g., $OCH_3$, $OCH_2CH_3$, or any alkyoxy chain with 3-10 carbon atoms, branched or unbranched), haloalkyl (e.g., $CH_2Cl$, $CHBr_2$, $CF_3$), haloalkoxyl (e.g., $OCH_2Cl$, $OCHBr_2$, $OCF_3$), a 1, 2, 3, 4, 5, 6, 7, 8, 9, or 10 carbon haloalkyl having e.g., 1 to 3 halogen atoms, a 1, 2, 3, 4, 5, 6, 7, 8, 9, or 10 carbon haloalkoxyl having, e.g., 1 to 3 halogen atoms, cycloalkyl, and halocycloalkyl, wherein the "C" ring comprises one, two, three, four, or five of said $R^3$ substituents substituted in any combination of said $R^3$ substituents and arranged in any pattern in the "C" ring including ortho, meta, para, mono, di, tri, tetra, and pentasubstituted.

In at least certain non-limiting embodiments, each $R^4$ and $R^5$ substituent of chemical structure I can selected from the group: H, F, Cl, Br, I, $NO_2$, alkyl (e.g., branched or unbranched, $C_1$ to $C_{10}$), and haloalkyl (e.g., $CH_2Cl$, $CHBr_2$, $CF_3$). $R^4$ and $R^5$ may together consist of a double bonded O.

In at least certain non-limiting embodiments, $R^4$ and $R^5$ together form a cycloalkyl comprising two to 10 carbon atoms, or a halocycloalkyl comprising two to 10 carbon atoms and substituted with one or more halogen (Cl, F, Br, I) atoms.

In at least certain embodiments, when one of $R^4$ and $R^5$ is an alkyl or cycloalkyl (as defined herein), the other of $R^4$ and $R^5$ is H.

In at least certain non-limiting embodiments, each $R^6$ and $R^7$ substituent of chemical structure I can selected from the group: H, F, Cl, Br, I, alkyl (e.g., branched or unbranched, $C_1$ to $C_{10}$), and haloalkyl (e.g., $CH_2Cl$, $CHBr_2$, $CF_3$). $R^6$ and $R^7$ may together consist of a double bonded O.

In at least certain non-limiting embodiments, $R^6$ and $R^7$ together form a cycloalkyl comprising two to 10 carbon atoms, or a halocycloalkyl comprising two to 10 carbon atoms and substituted with one or more halogen (Cl, F, Br, I) atoms.

In at least certain embodiments, when one of $R^6$ and $R^7$ is an alkyl or cycloalkyl (as defined herein), the other of $R^6$ and $R^7$ is H.

As noted, in certain embodiments, rings A and/or B and/or C of chemical structure I may be a pyridine. Schemes 1-3 below show exemplary, non-limiting, synthetic pathways which can be used to form structures of the present disclosure which comprise rings A and/or B as pyridines:

Scheme 1

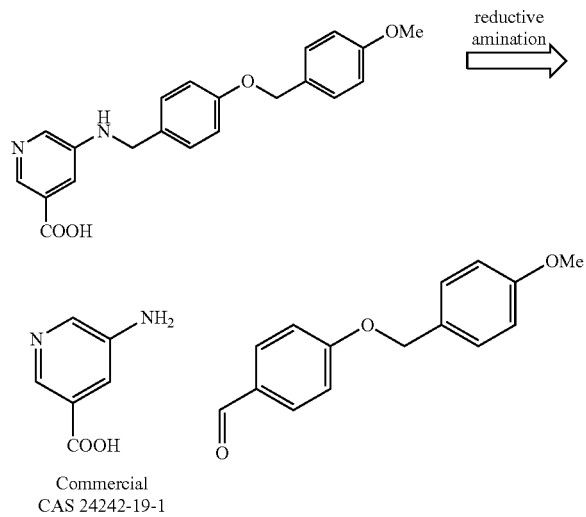

Commercial
CAS 24242-19-1

Schemes 2 and 3

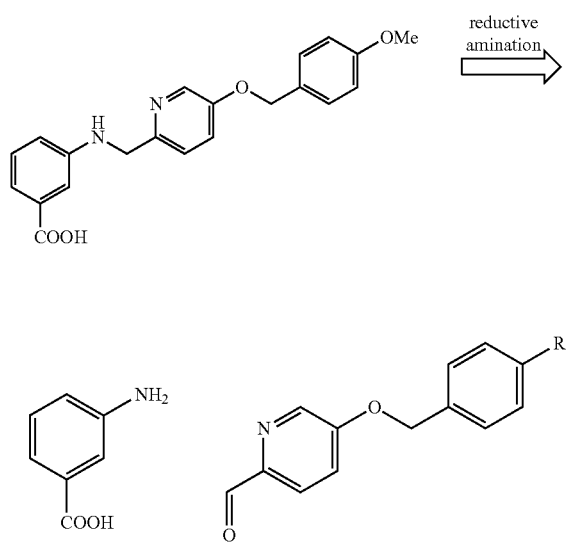

Commerical
R = H, CAS 59781-08-7
R = OMe, CAS 357613-17-3

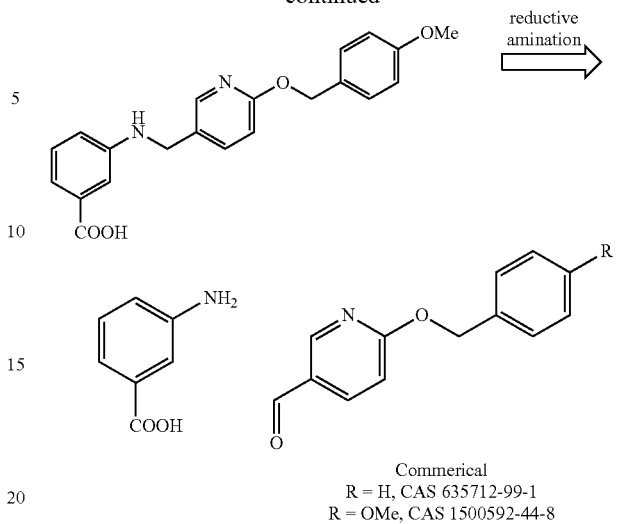

Commerical
R = H, CAS 635712-99-1
R = OMe, CAS 1500592-44-8

In at least certain alternate embodiments, the present disclosure includes active agent compositions and methods for treating ocular disorders and conditions, and particularly retinal conditions and disorders, which in certain non-limiting embodiments, include retinal inflammation, retinal neovascularization, retinal vascular leakage, retinopathy of prematurity (ROP), diabetic retinopathy (DR), age-related macular degeneration (e.g., wet AMD), and diabetic macular edema (DME) (or others disorders or conditions described elsewhere herein) using a compound having the chemical structure II:

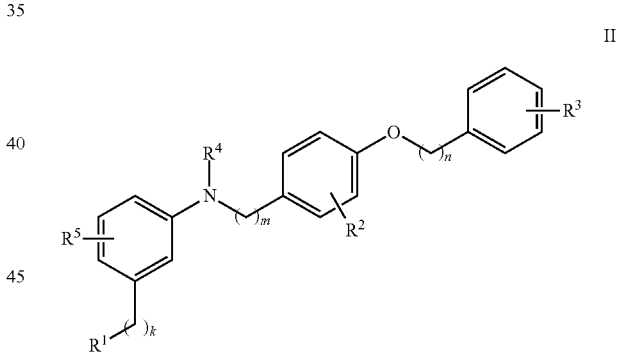

II wherein:
k is 0, 1, 2, 3, 4, 5, 6, 7, 8, 9, or 10 carbon atoms;
m is 0, 1, 2, 3, 4, or 5 carbon atoms;
n is 0, 1, 2, 3, 4, or 5 carbon atoms;
$R^2$ is selected from the group: hydrogen (H), chlorine (Cl), fluorine (F), bromine (Br), iodine (I), nitro ($NO_2$), $CH_3$, $CH_2CH_3$, branched or unbranched alkyl chains with 3-10 carbon atoms, $OCH_3$, $OCH_2CH_3$, branched or unbranched alkoxy chains with 3-10 carbon atoms, haloalkyls, haloalkoxyls, cycloalkyls, halocycloalkyls, O-para-alkyl-benzyls, O-para-alkyloxybenzyls, and O-para-halobenzyls, wherein the benzene ring comprising $R^2$ comprises one, two, three, or four of said $R^2$ substituents substituted in any combination of said $R^2$ substituents and arranged in any pattern in the ring including ortho, meta, mono, di, tri, and tetrasubstituted;
$R^3$ is selected from the group: H, Cl, F, Br, I, $NO_2$, $CH_3$, $CH_2CH_3$, branched or unbranched alkyl chains with 3-10 carbon atoms, $OCH_3$, $OCH_2CH_3$, branched or unbranched alkoxy chains with 3-10 carbon atoms, haloalkyls, haloalkoxyls, cycloalkyls, halocycloalkyls, O-para-alkylbenzyls, O-para-alkyloxybenzyls, and O-para-halobenzyls, wherein the benzene ring comprising $R^3$ comprises one, two, three, four, or five of said $R^3$ substituents substituted in any combination of said $R^3$ substituents and arranged in any pattern in the ring including ortho, meta, para, mono, di, tri, tetra, and pentasubstituted;

$R^4$ is selected from the group: H, alkyl, and acyl;

$R^5$ is selected from the group: H, Cl, F, Br, I, $NO_2$, $CH_3$, $CH_2CH_3$, branched or unbranched alkyl chains with 3-10 carbon atoms, $OCH_3$, $OCH_2CH_3$, branched or unbranched alkoxy chains with 3-10 carbon atoms, haloalkyls, haloalkoxyls, cycloalkyls, halocycloalkyls, O-para-alkylbenzyls, O-para-alkyloxybenzyls, and O-para-halobenzyls, wherein the benzene ring comprising $R^5$ comprises one, two, three, or four of said $R^5$ substituents substituted in any combination of said $R^5$ substituents and arranged in any pattern in the ring including ortho, meta, para, mono, di, tri, and tetrasubstituted;

$R^1$ is selected from the group consisting of carboxylic acids, carboxylic acid isosteres, hydroxamic acids, hydroxamic esters, phosphonic acids, phosphinic acids, sulfonic acids, sulfinic acids, sulfonamides, acyl sulfonamides, sulfonylureas, acylureas, tetrazoles, thiazolidine diones, oxazolidine diones, oxadiazol-5(4H)-ones, thiadiazol-5(4H)-ones, oxathiadiazole-2-oxides, oxadiazol-5(4H)-thiones, isoxazoles, tetramic acids, cyclopentane 1,3-diones, cyclopentane 1,2-diones, squaric acids, substituted phenols, heteroarenes, amidines, hydroxyamides, alkyl hydroxyamidines, and

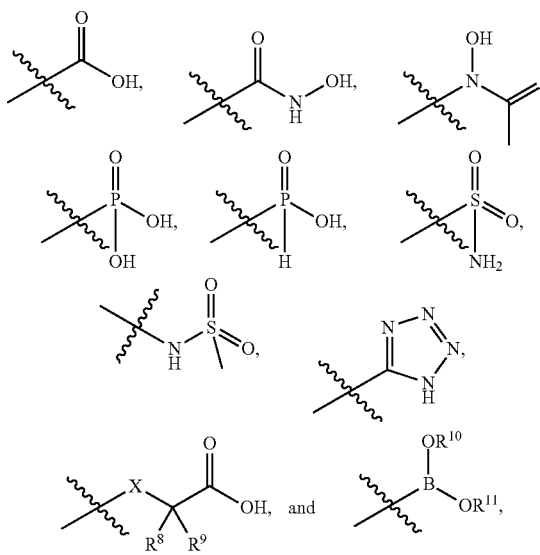

and salts thereof, $R^8$ and $R^9$ are independently selected from the group consisting of H, F, Cl, Br, I, alkyl, alkoxy, and cycloalkyl comprising $R^8$ is linked to $R^9$;

$R^{10}$ and $R^{11}$ are independently selected from the group consisting of H, alkyl, and cycloalkyl wherein $R^{10}$ is linked to $R^{11}$); and X is O, NH, S, or $CH_2$.

More particularly, in certain non-limiting embodiments of the present disclosure, examples of compounds having chemical structure II (compounds 9-14, 21-24, 26, and 28) are shown below:

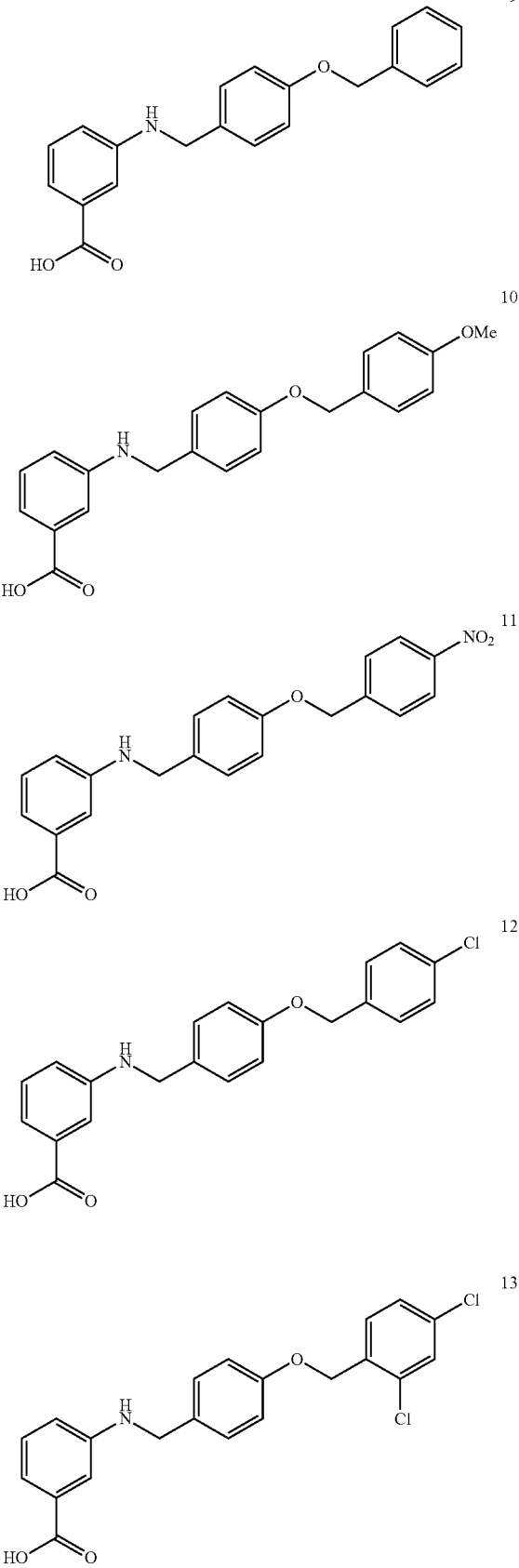

-continued
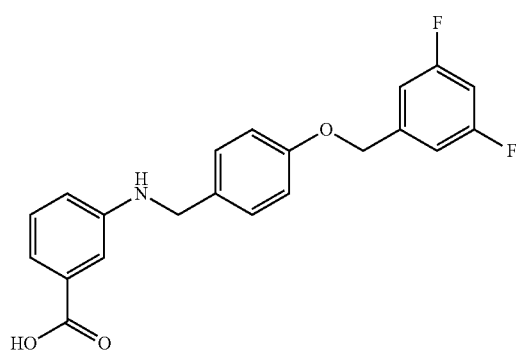
14
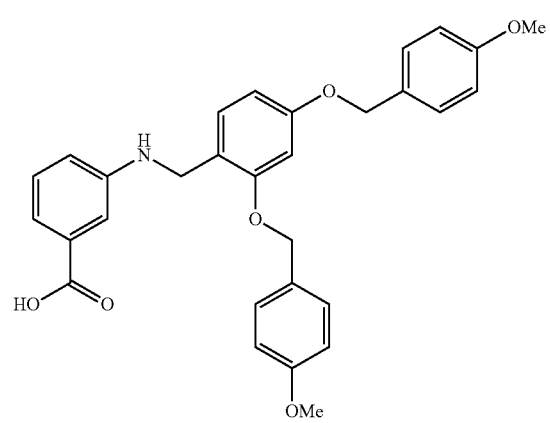
26
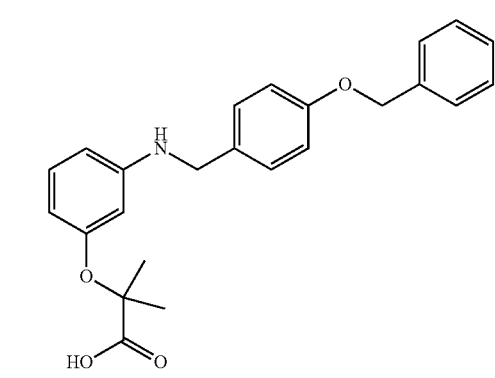
21
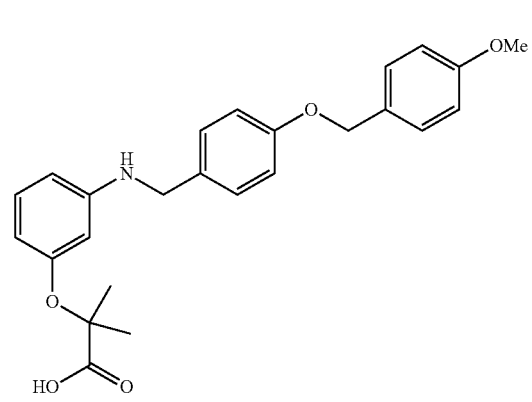
22
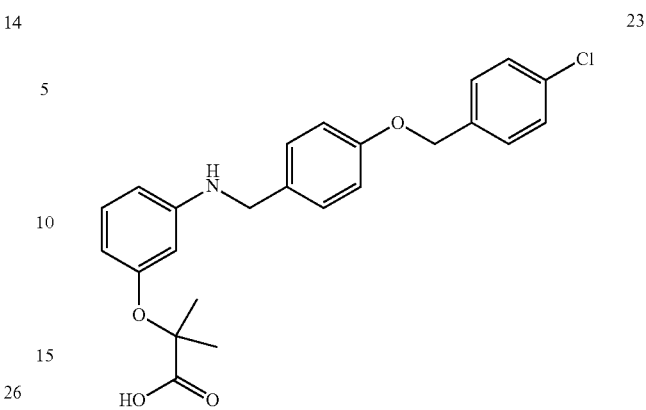
23
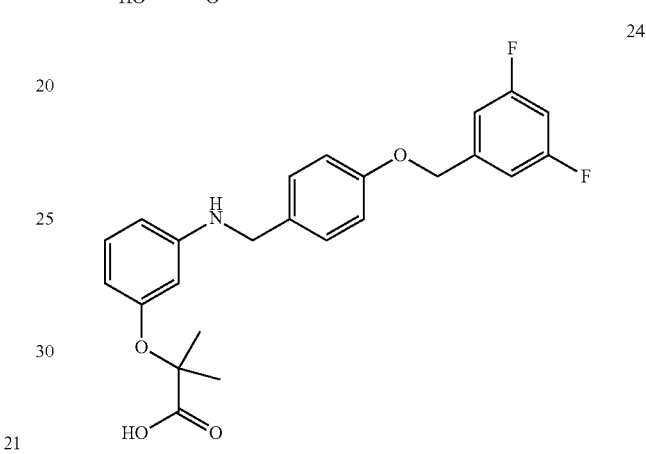
24
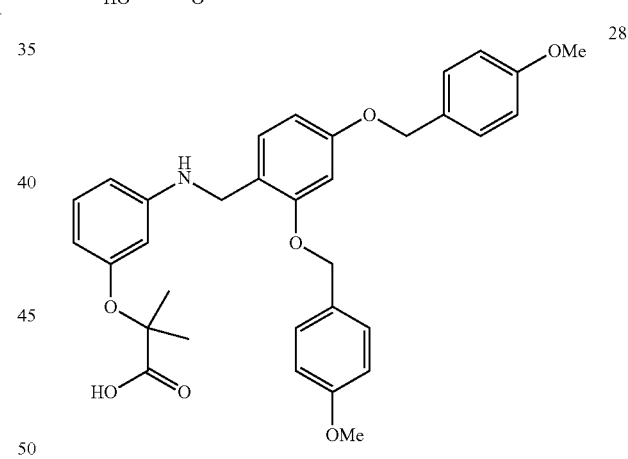
28
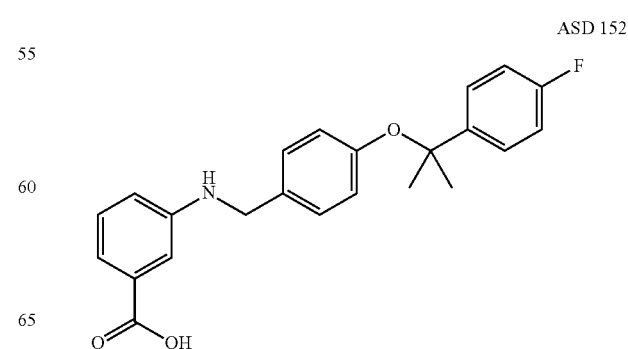
ASD 152

-continued

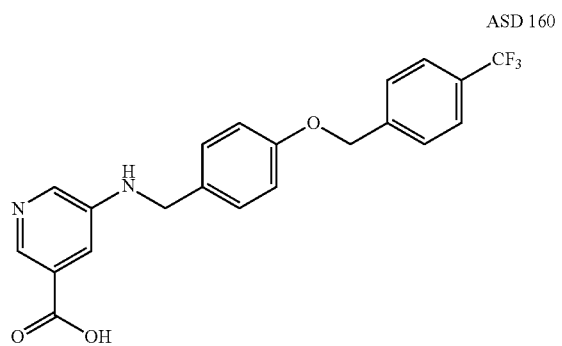

ASD 160

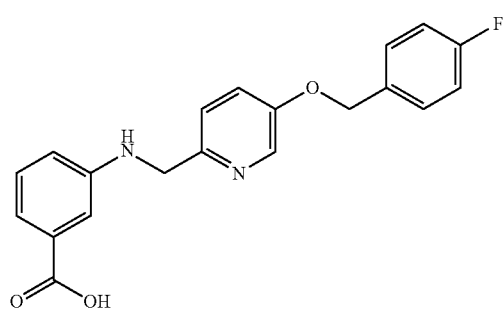

ASD 178

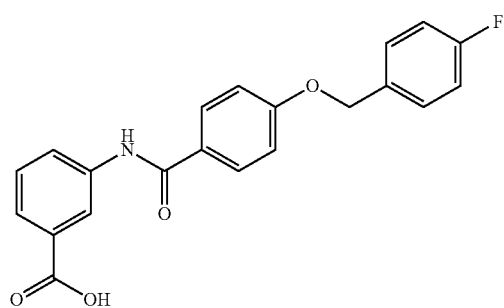

ASD 179

ASD 181

-continued

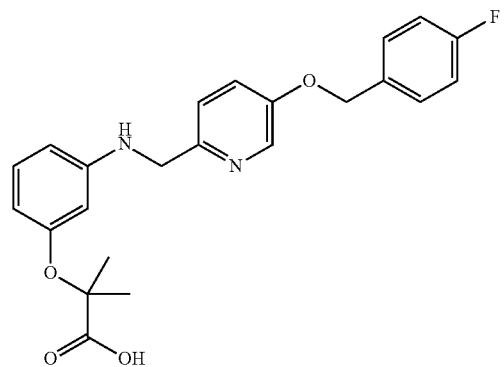

ASD 203

ASD 207

ASD 200

Compounds 9-14, 21-24, 26, and 28 are also numbered herein (e.g., in Tables 4 and 5) as 117, 91, 120, 122, 118, 119, 116, 114, 123, 121, 92, and 115, respectively. Compounds ASD152, ASD160, ASD178, ASD179, ASD181, ASD200, ASD203, and ASD207 are also referred to herein as compounds 152, 160, 178, 179, 181, 200, 203, and 207, respectively.

In certain embodiments, compounds (but not methods of the present disclosure), may exclude compounds having chemical structure II wherein (1) $R^1$=COOH, and $R^2$-$R^5$=H, and (2) $R^1$=COOH, $R^3$=CH$_3$, and $R^2$, $R^4$, and $R^5$=H, such as the structures:

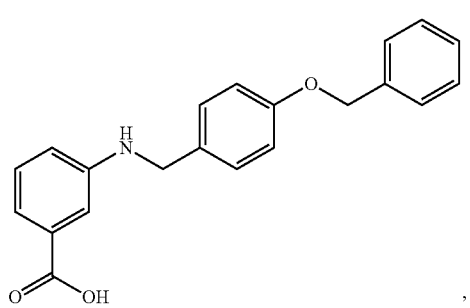

,

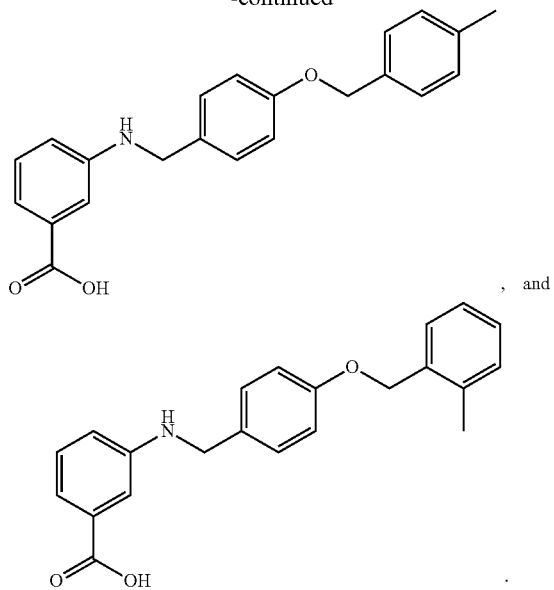
, and

Certain non-limiting embodiments of the present disclosure include pharmaceutical compositions that include at least one pharmaceutically acceptable carrier in combination with one or more compounds described herein that are agonists of PPARα and have anti-inflammatory and anti-angiogenic activities in the eye, particularly in the retina and macula. Particular non-limiting examples of pharmaceutical (therapeutic) compositions formulated in accordance with the present disclosure include: (a) a pharmaceutical composition comprising a PPARα agonist in combination with at least one pharmaceutically acceptable carrier, such as a polymer; and (b) a PPARα agonist in combination with at least one other therapeutically active agent, and at least one pharmaceutically acceptable carrier, such as a polymer.

As noted above, the active agents of the present disclosure can be used to treat diseases and conditions associated with retinal endothelial dysfunction, angiogenesis and inflammation, such as, for example, DR and AMD (e.g., wet AMD), retinal inflammation, retinal neovascularization (NV), retinal vascular leakage, retinopathy of prematurity (ROP), and diabetic macular edema (DME).

The active agents of the present disclosure may be present in the pharmaceutical compositions at any concentration that allows the pharmaceutical composition to function in accordance with the present disclosure; for example, but not by way of limitation, the compound(s) may be present in a range having a lower level selected from 0.0001%, 0.005%, 0.001%, 0.005%, 0.01%, 0.05%, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9% and 2.0%; and an upper level selected from 3%, 3.5%, 4%, 4.5%, 5%, 5.5%, 6%, 6.5%, 7%, 7.5%, 8%, 8.5%, 9%, 9.5%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, and 95%. Non-limiting examples of particular ranges include a range of from about 0.0001% to about 95%, a range of from about 0.001% to about 75%; a range of from about 0.005% to about 50%; a range of from about 0.01% to about 40%, a range of from about 0.05% to about 35%; a range of from about 0.1% to about 30%; a range of from about 0.1% to about 25%; a range of from about 0.1% to about 20%; a range of from about 1% to about 15%; a range of from about 2% to about 12%; a range of from about 5% to about 10%; and the like. Any other range that includes a lower level selected from the above-listed lower level concentrations and an upper level selected from the above-listed upper level concentrations also falls within the scope of the present disclosure.

Suitable carriers, vehicles, excipients, diluents, and other components that may be included in the formulation are described, for example, in *Remington: The Science and Practice of Pharmacy*, 21$^{st}$ Ed. and 22$^{nd}$ Ed. The term "pharmaceutically acceptable" means that the carrier is a non-toxic material that does not interfere with the effectiveness of the biological activity of the active agent. The characteristics of the carrier will depend on various factors, including but not limited to, the route of administration.

For example, but not by way of limitation, the active agents may be dissolved in a physiologically acceptable pharmaceutical carrier, vehicle, excipient, or diluent and administered as either a solution or a suspension. Non-limiting examples of suitable pharmaceutically acceptable carriers include water, saline, dextrose solutions, fructose solutions, ethanol, or oils of animal, vegetative, or synthetic origin, or any combination thereof. A sterile diluent, which may contain materials generally recognized for approximating physiological conditions and/or as required by governmental regulations, may be employed as the pharmaceutically acceptable carrier. In this respect, the sterile diluent may contain a buffering agent to obtain a physiologically acceptable pH, such as (but not limited to) sodium chloride, saline, phosphate-buffered saline, and/or other substances which are physiologically acceptable and/or safe for use.

The pharmaceutical compositions may also contain one or more additional components in addition to the active agents and pharmaceutically acceptable carrier(s) (and other additional therapeutically active agent(s), if present). Examples of additional components that may be present include, but are not limited to, diluents, fillers, salts, buffers, preservatives, stabilizers, solubilizers, and other materials well known in the art. Another particular non-limiting example of an additional component that may be present in the pharmaceutical composition is a delivery agent, as discussed in further detail herein below.

Other embodiments of the pharmaceutical compositions of the present disclosure may include the incorporation or entrapment of the active agents in various types of drug delivery systems that function to provide targeted delivery, controlled release, and/or increased half-life to the active agents. For example, but not by way of limitation, it is possible to entrap the active agents in microcapsules prepared by coacervation techniques or by interfacial polymerization (for example, hydroxymethylcellulose or gelatin-microcapsules and poly-(methylmethacylate) microcapsules, respectively). It is also possible to entrap the active agents in macroemulsions or colloidal drug delivery systems (such as but not limited to, liposomes, albumin microspheres, microemulsions, nanoparticles, nanocapsules, and the like). Such techniques are well known to persons having ordinary skill in the art, and thus no further description thereof is deemed necessary.

In one particular, non-limiting example, the pharmaceutical composition may include a liposome in which the active agent is disposed. In addition to other pharmaceutically acceptable carrier(s), the liposome may contain amphipathic agents such as lipids which exist in an aggregated form as micelles, insoluble monolayers, liquid crystals, or lamellar layers in aqueous solution. Suitable lipids for liposomal formulation include, but are not limited to, monoglycerides, diglycerides, sulfatides, lysolecithin, phospholipids, saponin, bile acids, combinations thereof, and the like. Preparation of such liposomal formulations is well within the level of ordinary skill in the art, as disclosed, for example, in U.S. Pat. Nos. 4,235,871; 4,501,728; 4,837,028; and 4,737,323; the entire contents of each of which are incorporated herein by reference.

In other non-limiting examples, the active agents of the present disclosure may be incorporated into particles of one or more polymeric materials, as this type of incorporation can be useful in controlling the duration of action of the active agents by allowing for controlled release from the preparations, thus increasing the half-life thereof. Non-limiting examples of polymeric materials that may be utilized in this manner include polyesters, polyamides, polyamino acids, hydrogels, poly(lactic acid-glycolic acid), poly(lactic acid), ethylene vinylacetate copolymers, copolymer micelles of, for example, PEG and poly(1-aspartamide), and combinations thereof.

In certain non-limiting embodiments, the pharmaceutical composition containing the active agents may be in the form of an ophthalmic composition for topical application to an eye of a subject. The term "ophthalmic composition" as used herein will be understood to refer to any composition specifically formulated for direct and local administration to an eye of a patient. Said composition may be formulated for topical administration to the eye or for injection into the eye (i.e., intravitreal or intraocular injection). The ophthalmic composition may be provided in any formulation that allows for local administration thereof to the eye and allows the active agents to function in accordance with the present disclosure. For example, but not by way of limitation, the ophthalmic composition may be provided in the form of a solution, drops, a mist/spray, plasters and pressure sensitive adhesives, an ointment, a lotion, a cream, a gel, lyophilized/spray-dried forms, and the like. In one particular non-limiting embodiment, the ophthalmic composition is provided in a form for topical application, such as but not limited to, an eyedrop formulation. The ophthalmic compositions of the present disclosure may vary according to the particular active agent(s) used, the desired drug release profile, the condition being treated, and/or the medical history of the patient. In addition, the ophthalmic compositions of the present disclosure may be designed to provide delayed, controlled, extended, and/or sustained release using formulation techniques which are well known in the art, and as explained elsewhere herein.

The pharmaceutical compositions described or otherwise contemplated herein may further comprise at least one delivery agent that assists in delivery of the active agents to a desired site of delivery; for example but not by way of limitation, at least one delivery agent may be included in an ophthalmic composition to assist in the penetration of a surface of an eye; in certain embodiments, the delivery agent may assist in delivery to a retina of the eye. For example, in order for a topical application to be effective, the composition may need to be able to penetrate the surface of the eye so that it can travel to the desired tissue. This may include penetrating the conjunctiva and/or the cornea.

When the ophthalmic composition containing the active agent(s) is formulated for administration by injection, the composition may be in the form of a pyrogen-free, aqueous solution or suspension. The preparation of such solutions, having due regard to pH, isotonicity, stability, and the like, is well within the skill of one of ordinary skill in the art. Suitable carriers include, but are not limited to, biocompatible and pharmaceutically acceptable phosphate buffered saline solutions, which are particularly isotonic. For example, but not by way of limitation, a particular ophthalmic composition may contain, in addition to the therapeutic compound(s), an isotonic vehicle such as Sodium Chloride Injection, Ringer's Injection, Dextrose Injection, Dextrose and Sodium Chloride Injection, Lactated Ringer's Injection, or other vehicles as known in the art. In general, the material for intravenous injection in humans should conform to regulations established by the US Food and Drug Administration, which are available to those in the field.

In addition to the ophthalmic administrations discussed in detail herein above, the therapeutic compositions of the present disclosure may be formulated for administration by any other method known or otherwise contemplated in the art, as long as the route of administration allows for delivery of the active agent(s) so that the compounds can function in accordance with the present disclosure, i.e., as a PPARα agonist. Examples of other routes of administration include, but are not limited to, oral, topical, retrobulbar, subconjunctival, transdermal, parenteral, subcutaneous, intranasal, intramuscular, intraperitoneal, intravitreal, and intravenous routes, including both local and systemic application routes.

Another non-limiting embodiment of the present disclosure is directed to a kit that contain one or more of any of the pharmaceutical compositions described or otherwise contemplated herein. The kit may further contain a second agent as described herein above for use concurrently with the pharmaceutical composition(s). If the composition present in the kit is not provided in the form in which it is to be delivered, the kit may further contain a pharmaceutically (e.g., ophthalmically) acceptable carrier, vehicle, diluent, excipient, or other agent for mixing with the active agent(s) for preparation of the pharmaceutical composition. The kit including the composition and/or other reagents may also be packaged with instructions packaged for administration and/or dosing of the compositions contained in the kit. The instructions may be fixed in any tangible medium, such as printed paper, or a computer-readable magnetic or optical medium, or instructions to reference a remote computer data source such as a worldwide web page accessible via the internet.

The kit may contain single or multiple doses of the pharmaceutical composition(s). When multiple doses are present, the doses may be disposed in bulk within a single container, or the multiple doses may be disposed individually within the kit; that is, the pharmaceutical compositions may be present in the kit in unit dosage forms to facilitate accurate dosing. The term "unit dosage forms" as used herein refers to physically discrete units suitable as unitary dosages for human subjects and other mammals; each unit contains a predetermined quantity of active material calculated to produce the desired therapeutic effect, in association with a suitable pharmaceutical excipient. Typical unit dosage forms of liquid compositions include prefilled, premeasured ampules or syringes; for solid compositions, typical unit dosage forms include pills, tablets, capsules, or the like. In such compositions, the active agent(s) may sometimes be a minor component (from about 0.1 to about 50% by weight, such as but not limited to, from about 1 to about 40% by weight) with the remainder being various vehicles or carriers and processing aids helpful for forming the desired dosing form.

As is evident from the above, the active agent(s) of the present disclosure function as PPARα agonists for the treatment, inhibition, mitigation, and/or prevention of degenerative retinal disorders. Thus, certain non-limiting embodiments of the present disclosure include methods of treating, inhibiting, and/or reducing the occurrence of retinal degeneration due to retinal inflammation and neovascularization. One particular but non-limiting embodiment includes a method of treating, inhibiting, and/or reducing the occurrence of one or more pathologic ocular conditions associated with reduced PPARα activity in a subject. In the method, one or more of any of the active agent(s) or pharmaceutical compositions described or otherwise contemplated herein is administered to a subject (such as, but not limited to, a mammal) that is experiencing retinal or macular degeneration or that is predisposed to developing retinal or macular degeneration, or other ocular condition or disorder. The active agent(s) or pharmaceutical composition(s) is administered to the subject in an amount effective to have PPARα agonistic activity in the retina of at least one eye of the subject.

The pathologic ocular condition may be any of the conditions described herein, and the pathologic ocular condition may be characterized by retinal and/or macular degeneration. In one embodiment, the pharmaceutical composition may be administered topically to an eye of the subject (such as, but not limited to, as an eyedrop). In an alternative embodiment, the pharmaceutical composition may be administered by ocular injection, or systemically.

The amount of the active agent(s) that is effective in the treatment described herein can be determined by the attending diagnostician, as one of ordinary skill in the art, by the use of conventional techniques and by observing results obtained under analogous circumstances. For example, in one non-limiting embodiment of a treatment, in determining the therapeutically effective dose, a number of factors may be considered by the attending diagnostician, including, but not limited to: the species of the subject; its size, age, and general health; the specific disease and/or condition involved; the degree, involvement, and/or severity of the disease and/or condition; the response of the individual subject; the particular active agent(s) or other therapeutic compound(s) administered; the mode of administration; the bioavailability characteristics of the preparation administered; the dose regimen selected; the use of concomitant medication; and other relevant circumstances. A therapeutically effective amount of a pharmaceutical composition of the present disclosure also refers to an amount of the active agent(s) which is effective in controlling and/or reducing or ameliorating the disease and/or condition.

For example, but not by way of limitation, the therapeutically effective amount of a active agent(s) used in the present disclosure will generally contain sufficient active ingredient to deliver in a range of from about 0.01 μg/kg to about 10 mg/kg (weight of active ingredient/body weight of patient). For example, but not by way of limitation, the composition will deliver about 0.1 μg/kg to about 5 mg/kg, and more particularly about 1 μg/kg to about 1 mg/kg.

Practice of the method of the present disclosure may include administering to a subject a therapeutically effective amount of the pharmaceutical composition (containing the active agent(s)) in any suitable systemic and/or local formulation, in an amount effective to deliver the dosages listed above. The dosage can be administered, for example, but not by way of limitation, on a one-time basis, or administered at multiple times (for example, but not by way of limitation, from one to five times per day, or once or twice per week). The pharmaceutical composition may be administered either alone or in combination with other therapies, in accordance with the inventive concepts disclosed herein.

Certain novel embodiments of the present disclosure, having now been generally described, will be more readily understood by reference to the following examples, which are included merely for purposes of illustration of certain aspects and embodiments of the present disclosure, and are not intended to be limiting. The following detailed examples are to be construed, as noted above, only as illustrative, and not as limiting of the present disclosure in any way whatsoever. Those skilled in the art will promptly recognize appropriate variations from the various compositions, structures, components, procedures and methods.

EXAMPLES

The anti-inflammatory and anti-angiogenic activities of certain active agent(s) disclosed herein were investigated. Prior to the present work, none of the compounds described herein have been reported to have PPAR agonist activity, except 7-chloro-8-methyl-2-phenylquinoline-4-carboxylic acid (designated herein as Y-0452), fenofibrate, GW409544, and GW590735, shown directly below:

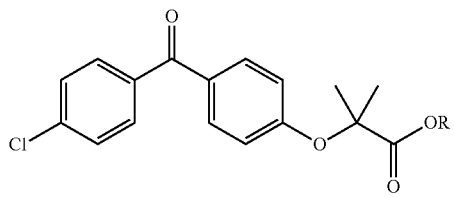

Fenofibrate, R = i-pr
Fenofibric Acid, R = OH

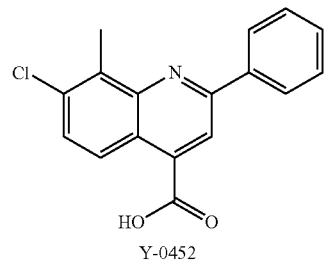

Y-0452

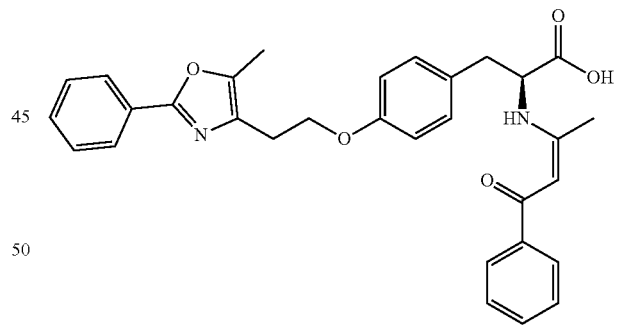

GW409544

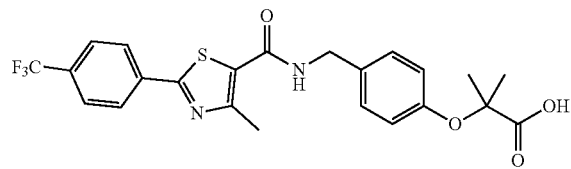

GW590735

A series of derivatives bearing some structural similarity to Y-0452 were evaluated for PPARα agonism. Compounds 9-14 and 21-24 were designed with an aim to fill a hydrophobic binding pocket in the PPARα more efficiently.

Derivatives 9-14 were synthesized as shown in Scheme 4. Commercially available 4-hydroxybenzaldehyde was coupled with various benzyl bromides 3-8 to afford benzaldehydes 3a-8a. Treatment of 3a-8a with 3-aminobenzoic acid produced the respective imines in situ, which were then reduced upon the addition of sodium triacetoxyborohydride to provide 9-14 in an unoptimized 40-82% yield.

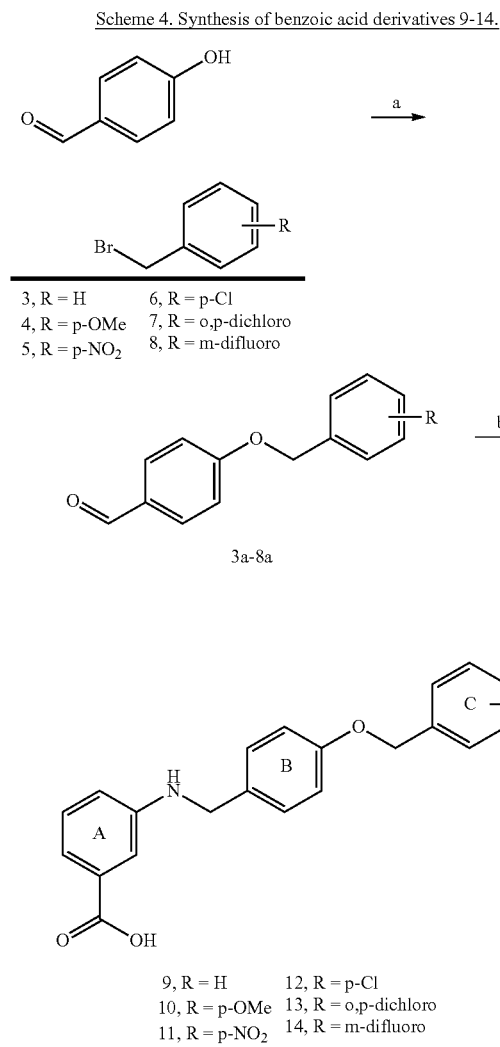

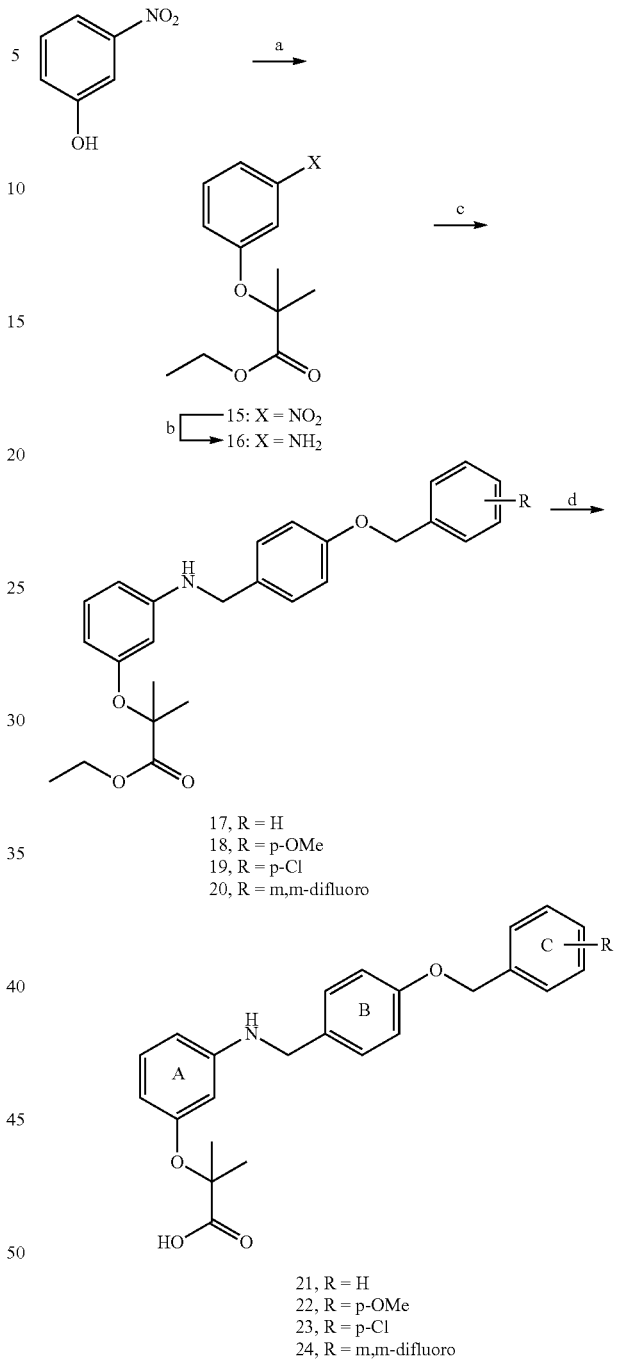

In addition to the benzoic acids derivatives 9-14, we wanted to incorporate the classical "head-group" of fenofibrate an aim to improve potency and instill selectivity for PPARα over other isoforms. The preparation of these analogs is depicted in Scheme 5. Commercially available 3-nitrophenol was coupled with ethyl α-bromoisobutyrate to afford 15, which was then reduced to the corresponding aniline (16) under catalytic hydrogenation conditions ($H_2$ and Pd/C in ethanol). Treatment of 16 with 3a, 4a, 6a, or 8a followed by reduction with sodium triacetoxyborohydride yielded 17-20, respectively. Hydrolysis of the pendant ester gave the desired products 21-24 in an unoptimized 46-88% yield.

With the focused subset of analogs in-hand, our efforts shifted to the evaluation of these derivatives for PPARα agonism. Preliminary evaluation utilized a commercially available PPARα luciferase cell reporter assay (Indigo Biosciences). The cell-line employed is engineered to constitutively express high-levels of hPPARα. Upon interaction with an agonist, hPPARα translocates to the nucleus, binds to the PPRE, and upregulates gene transcription, including the inserted luciferase gene. Luciferase activity is detected indirectly through quantification of oxyluciferin production. Initially, 9-14 and 21-24 were evaluated at 5 M and 50 µM to provide an idea of agonism-level at two 10-fold increments. As shown in FIG. 1, a number of compounds exhibited levels of hPPARα agonism on par with or surpassing the positive control, GW590735 (5 µM and 10 µM), at one or both of the concentrations evaluated. Direct comparison of 9/21, 10/22, 12/23, 14/24 reveals that incorporation of the fenofibrate "head-group" enhances the level of PPARα agonism at 50 µM. This data also indicates, however, that incorporation of the fenofibrate "head-group" decreases potency, as 21-24 fail to elicit appreciable activity at 5 M, whereas the benzoic acid analogs 9-14 all exhibit significant PPARα agonism at this lower concentration. Compounds 10 and 22 were selected for more detailed evaluation, and a more expansive 10-point dose-response assessment was conducted to obtain $EC_{50}$ values (Table 3): 10 (5.6 µM), and 22 (25.3 µM).

Figure 2A:
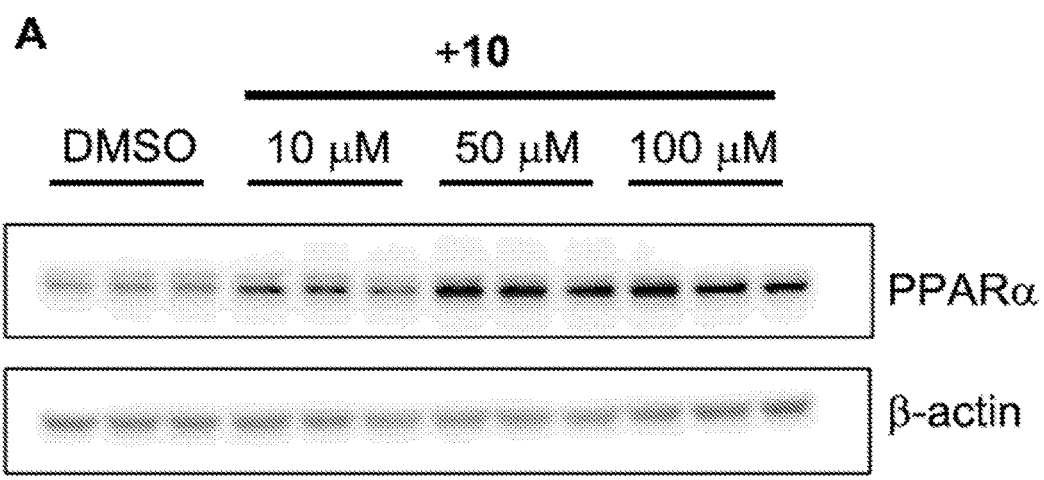
FIG. 2A shows a Western blot analysis of mouse 661 W cells after 24 h treatment with 10 μM, 50 μM and 100 μM of compound 10.
Figure 2B:
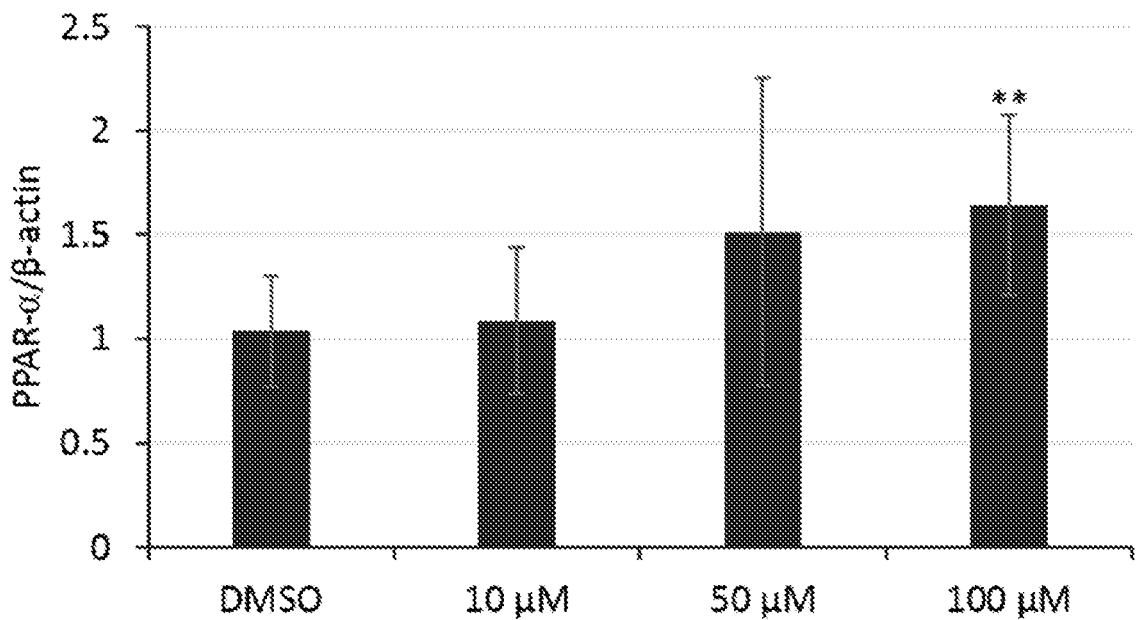
FIG. 2B shows results of a densitometry quantification of PPARα production from the Western blot analysis of FIG. 2A.
Figure 2C:
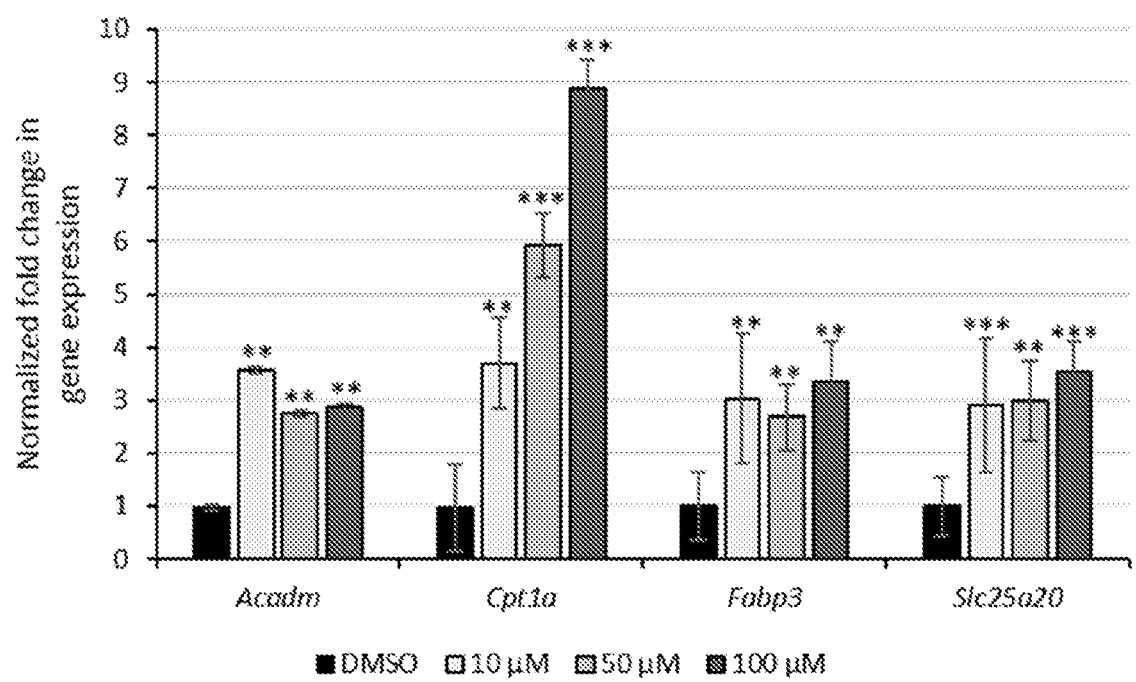
FIG. 2C shows a Real Time PCR analysis of mouse 661 W cells after 24 h (n=6) treatment with compound 10.
Figure 2D:
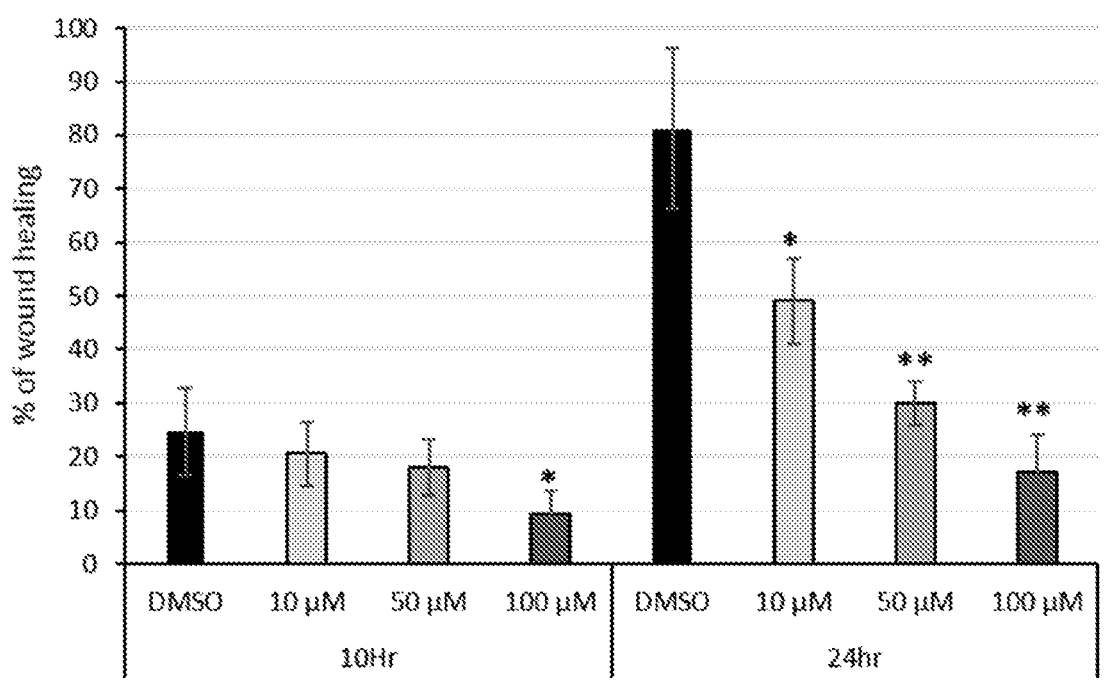
FIG. 2D shows HRCEC wound healing assay results for both 10 h and 24 h incubation time points with compound 10. Experiments in FIGS. 2A-D were performed three times in triplicate unless otherwise noted. All values shown are expressed as mean±S.D. Differences between groups were tested for statistical significance using the Student's t-test. *P<0.05, P<0.01, *P<0.001.

To further confirm that this 4-benzyloxy-benzylamino chemotype acts as a PPARα agonist, we evaluated compound 10 in various biochemical assays. As expected for a PPARα agonist, 10 induced the expression of PPARα in a dose-dependent manner (FIGS. 2A and 2B), as demonstrated by Western blot analysis using a cell line derived from $C_{57}BL/6N$ mouse photoreceptors (661 W). Likewise, RT-PCR studies on the same cell-line confirm PPAR agonism, as treatment with 10 induces the expression of various PPARα target genes (FIG. 2C), including acyl-CoA dehydrogenase medium chain (Acadm), carnitine palmitoyltransferase 1A (Cpt1a), fatty acid binding protein 3 (Fabp3), and solute carrier family 25 member 20 (Slc25a20). Compound 10 was also evaluated in an in vitro wound healing assay utilizing human retinal capillary endothelial cells (HRCEC). PPARα agonism reduces cell migration[12] and 10, indeed, inhibits wound closure in a dose-dependent fashion (FIG. 2D).

With the evidence that 4-benzyloxy-benzylamino derivatives exhibited characteristic PPARα agonistic activity in several biological settings, the selectivity of 10 for PPARα agonism over PPARδ and PPARγ was assessed. Luciferase assays were conducted on isogenic cell-lines engineered to overexpress either PPARδ or PPARγ with expression of the requisite luciferase reporter gene dependent upon exogenous activation of each isoform. As shown in Table 3, compound 10 exhibits ≥20-fold selectivity for hPPARα over hPPARδ and hPPARγ, whereas 22 displays pan-agonism. This is interesting, as the fibrate "head-group" has been described as a critical feature for PPAR selectivity, but with this 4-benzyloxy-benzylamino chemotype it seems to be detrimental.

TABLE 3

Human PPAR agonism of select analogs.

| Compound No. | hPPARα $EC_{50}(\mu M)$ | hPPARδ $EC_{50}(\mu M)$ | hPPARγ $EC_{50}(\mu M)$ |
|---|---|---|---|
| 10 | 5.6(1.5) | >100 | >100 |
| 22 | 25.3(1.7) | 38.6 | 18.3 |
| 26 | 5.1(1.1) | >100 | >100 |
| 28 | 2.1(1.4) | 8.9 | 5.6 |
| GW590735 | 0.012 | n.d. | n.d. |

TABLE 3-continued

Human PPAR agonism of select analogs.

| Compound No. | hPPARα $EC_{50}(\mu M)$ | hPPARδ $EC_{50}(\mu M)$ | hPPARγ $EC_{50}(\mu M)$ |
|---|---|---|---|
| Rosiglitazone | n.d. | n.d. | 0.083 |
| GW0742 | n.d | 0.002 | n.d. |
| Y-0452 | 52.4 (0.3) | n.d. | n.d. |

Data are represented as the $EC_{50}$ (µM) for the agonism of the corresponding luciferase reporter cell-lines (Indigo Biosciences). Dosing was done in triplicate as a single experiment.
n.d. = not determined. Values in parentheses indicate the ratio of agonism compared to GW590735.

Figure 3:
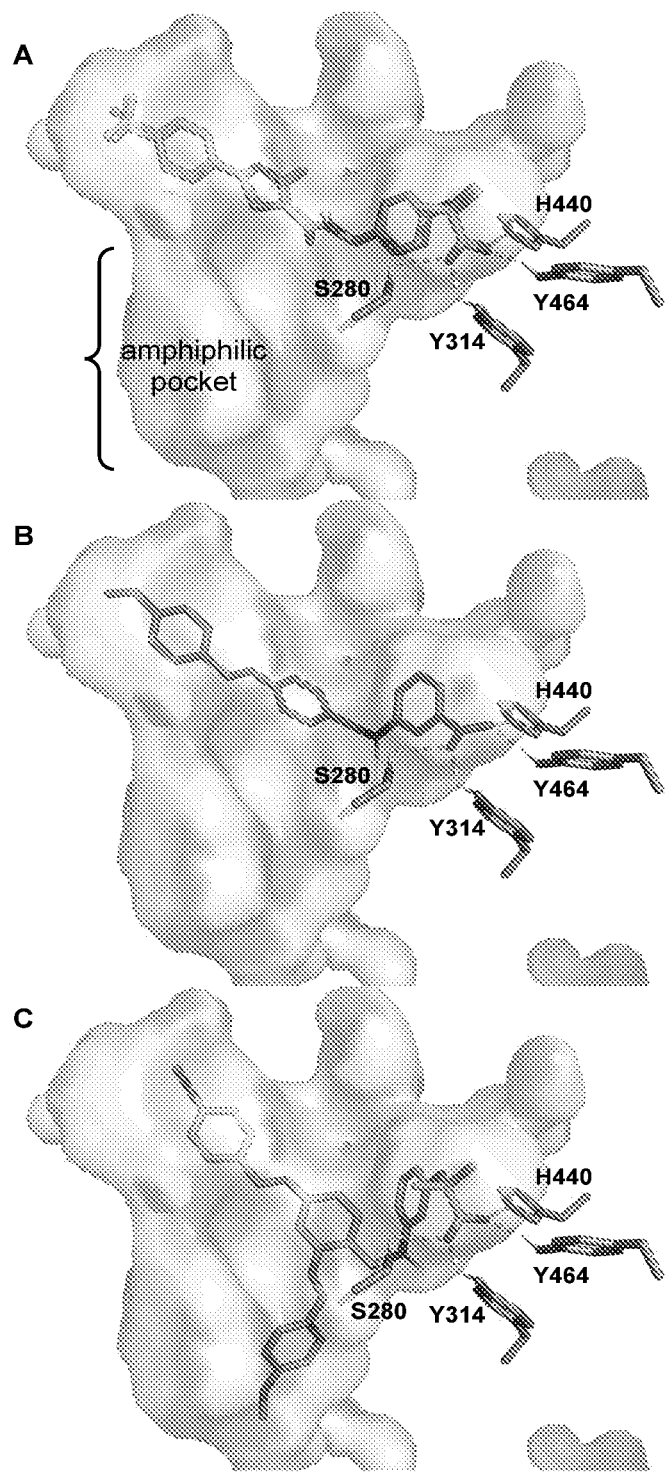
FIG. 3 shows (A) the GW590735•hPPARα co-crystal structure, (B) the predicted binding pose of 10 hPPARα, and (C) the predicted binding pose of compound 28 on hPPARα. Binding pocket cavity depicted by surface representation, PDB: 2P54.

To better visualize the 4-benzyloxy-benzylamino derivatives in the hPPARα binding pocket, we utilized PDB 2P54, the GW590735•hPPARα co-crystal structure, for docking assessment. GW590735 is a selective PPARα agonist that exhibits ≥500-fold selectivity for PPARα over PPARγ and PPARδ. Without wishing to be bound by theory, as shown in FIGS. 3A and 3B, compound 10 is predicted to bind in an orientation similar to GW590735. Interestingly, however, 10 lacks the gem-dimethyl "head-group" and amide linker domain, both of which previously have been postulated to be critical determinants in GW590735 selectivity and major enhancers of potency. The acid, however, for 10 is predicted to make four hydrogen bonds with Ser280, Tyr314, His440, and Tyr464, consistent with the idea that deconstruction of the Y-0452 quinoline core and transposition of the carboxylic acid would provide a significant improvement in PPARα agonism. We were interested if this 4-benzyloxy-benzylamino chemotype could be expanded to take advantage of an apparent amphiphilic pocket that lies below GW590735 (FIG. 3A) and is comprised of Met330, Tyr334, Glu282, Thr279, Met320, Val324, Leu321, Ile317, and Met220. We postulated that functionalization of the B-ring meta to the ether linkage (Schemes 5 and 6) on 10 would provide an optimal trajectory for accessing this amphiphilic pocket. To the best of our knowledge, few PPAR agonists exploit this pocket and little SAR exists regarding the effect of occupying this domain on the level of agonism and/or isoform selectivity.

To investigate the possible impact of occupying the amphiphilic pocket, we synthesized two additional derivatives, 26 and 28 (Scheme 6). Briefly, commercially available 2,4-dihydroxybenzaldehyde was treated with 4-methoxybenzaldehyde in the presence of potassium carbonate in acetone to produce the di-p-methoxybenzyl (PMB) functionalized resorcinol 25. This intermediate was coupled to either 3-aminobenzoic acid or 16 followed by reduction of the resulting imine to provide analog 26 and the methyl ester 27, respectively. Following saponification of 27, the desired derivative 28 was obtained in 75% yield. Incorporation of the 4-methoxybenzyl motif as the "third-arm" was rather arbitrary at this point and was selected on belief that it 1) would be compatible with the predicted binding environment and 2) could be easily synthesized through dialkylation of an aldehyde already in our chemical inventory.

Scheme 6. Synthesis of derivatives 26 and 27.

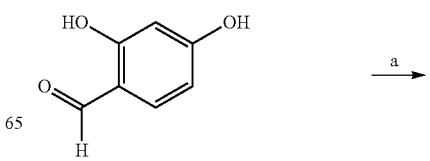

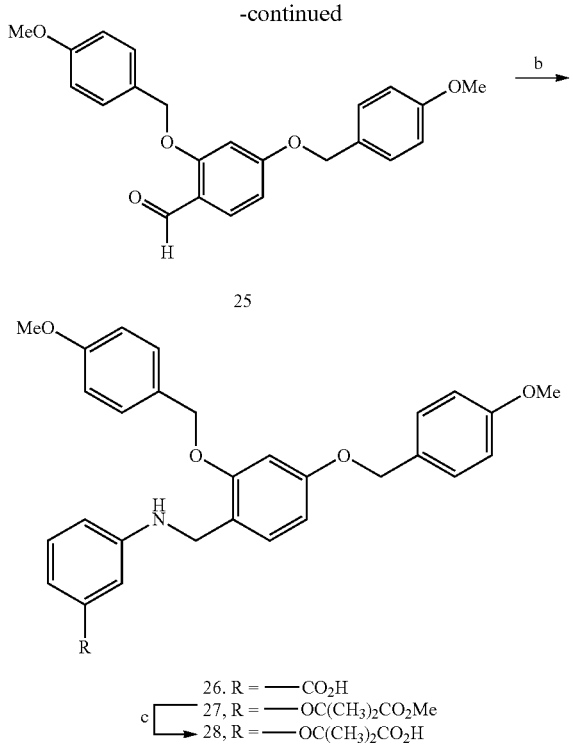

25

26. R = —CO$_2$H
27. R = —OC(CH$_3$)$_2$CO$_2$Me
28. R = —OC(CH$_3$)$_2$CO$_2$H

Reagents and conditions: (a) 4-methoxybenzyl bromide, K$_2$CO$_3$, Acetone; (b) 3-aminobenzoic acid or 16 toluene, 155° C., 2 h; sodium triacetoxyborohydride, AcOH, THF, 0° C. to 25° C., 12 h; (c) LiOH•H$_2$O, THF/MeOH/H$_2$O, 12 h.

Derivatives 26 and 28 were evaluated for hPPARα agonistic activity and selectivity in the luciferase cell-lines. Analysis of the data suggests that regarding the benzoic acid derivatives (compare 10 and 26), the additional 4-methoxybenzyl substituent does not affect potency and maintains the selectivity, at least within the range of doses evaluated. For derivatives containing the fibrate "head-group" (compare 22 and 28), however, the addition of the third substituent on the B-ring resulted in a 10-fold improvement in potency, but the pan-agonist profile was maintained. Both 26 and 28 were docked using our previously generated model and as can be seen in FIG. 3C the additional 4-methoxybenzyl group is, indeed, predicted to extend into the amphiphilic pocket.

Various non-limiting embodiments of the compounds of the present disclosure and their cellular luciferase activities are shown in Tables 4-7. Chemical structure IIa (Tables 4 and 5) is a version of chemical structure II in which k=0. Chemical structure IIb (Tables 6 and 7) is version of chemical structure IIa wherein the R$^1$ group is in the para position on Ring A.

Structure IIa

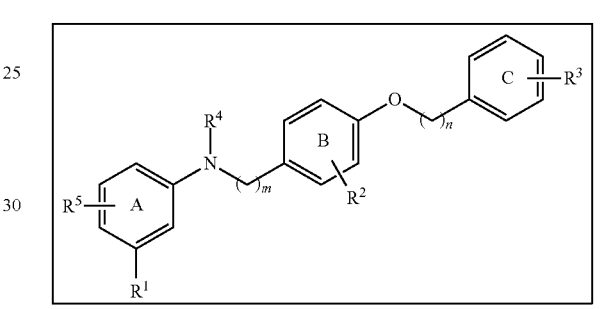

TABLE 4

Representative Examples of Compounds having Chemical Structure IIa

| R$^1$ | R$^4$ | m | n | R$^3$ | R$^2$ | R$^5$ | Compound No. (Alternate no.) |
|---|---|---|---|---|---|---|---|
| COOH | H | 1 | 1 | 4-OCH$_3$ | H | H | 91, (10) |
| COOH | H | 1 | 1 | 4-OCH$_3$ | 3-OPMB[1] | H | 92, (26) |
| B(OH)$_2$ | H | 1 | 1 | 4-OCH$_3$ | H | H | 110 |
| OC(CH$_3$)$_2$COOH | H | 1 | 1 | 4-OCH$_3$ | H | H | 114, (22) |
| OC(CH$_3$)$_2$COOH | H | 1 | 1 | 4-OCH$_3$ | 3-OPMB[1] | H | 115, (28) |
| OC(CH$_3$)$_2$COOH | H | 1 | 1 | H | H | H | 116, (21) |
| COOH | H | 1 | 1 | H | H | H | 117, (9) |
| COOH | H | 1 | 1 | 2,4-dichloro | H | H | 118, (13) |
| COOH | H | 1 | 1 | 3,5-difluoro | H | H | 119, (14) |
| COOH | H | 1 | 1 | 4-NO$_2$ | H | H | 120, (11) |
| OC(CH$_3$)$_2$COOH | H | 1 | 1 | 3,5-difluoro | H | H | 121, (24) |
| COOH | H | 1 | 1 | 4-Cl | H | H | 122, (12) |
| OC(CH$_3$)$_2$COOH | H | 1 | 1 | 4-Cl | H | H | 123, (23) |
| COOH | H | 1 | 1 | 4-F | H | H | 125 |
| COOH | H | 1 | 1 | 4-CF$_3$ | H | H | 126 |
| OC(CH$_3$)$_2$COOH | H | 1 | 1 | 4-F | H | H | 127 |
| OC(CH$_3$)$_2$COOH | H | 1 | 1 | 4-CF$_3$ | H | H | 128 |
| OCH$_2$COOH | H | 1 | 1 | 4-CF$_3$ | H | H | 129 |
| OCH$_2$COOH | H | 1 | 1 | 4-OCH$_3$ | H | H | 130 |
| COOH | H | 2 | 2 | H | H | H | 133 |
| C(O)NHOH | H | 1 | 1 | 4-OCH$_3$ | H | H | 134 |
| NHSO$_2$CH$_3$ | H | 1 | 1 | 4-F | H | H | 145 |
| C(O)NHOH | H | 1 | 1 | 4-F | H | H | 146 |
| SO$_2$NH$_2$ | H | 1 | 1 | 4-F | H | H | 147 |
| tetrazole | H | 1 | 1 | 4-F | H | H | 148 |

TABLE 4-continued

Representative Examples of Compounds having Chemical Structure IIa

| R$^1$ | R$^4$ | m | n | R$^3$ | R$^2$ | R$^5$ | Compound No. (Alternate no.) |
|---|---|---|---|---|---|---|---|
| COOH | CH$_3$ | 1 | 1 | 4-F | H | H | 151 |
| OC(CH$_3$)$_2$COOH | CH$_3$ | 1 | 1 | 4-F | H | H | 153 |
| B(OH)$_2$ | H | 1 | 1 | 4-F | H | H | 154 |
| COOH | H | 1 | 1 | 4-F | H | 4-F | 158 |
| COOH | H | 1 | 1 | 4-OCH$_3$ | H | 4-F | 159 |
| COOH | H | 1 | 1 | 4-F | H | 5-Cl | 168 |
| COOH | H | 1 | 1 | 4-F | H | 6-CH$_3$ | 174 |
| COOH | H | 1 | 1 | 4-F | H | 5-Br | 184 |
| COOH | H | 1 | 1 | 4-F | H | 5-F | 185 |
| COOH | H | 2 | 2 | 4-OCH$_3$ | H | H | 187 |
| SC(CH$_3$)$_2$COOH | H | 1 | 1 | 4-F | H | H | 188 |
| COOH | H | 1 | 1 | 4-I | H | H | 189 |
| COOH | H | 1 | 1 | 4-F | 2-CH$_3$ | H | 190 |
| COOH | H | 1 | 1 | 4-CN | H | H | 191 |
| COOH | H | 1 | 1 | 4-Br | H | H | 192 |
| COOH | H | 1 | 1 | 3-F | H | H | 193 |
| COOH | H | 1 | 1 | 2,4-difluoro | H | H | 194 |
| COOH | H | 1 | 1 | 2-F | H | H | 195 |
| COOH | H | 1 | 1 | 2,4-difluoro | 2-CH$_3$ | H | 196 |
| COOH | H | 1 | 1 | 3,4-difluoro | 2-CH$_3$ | H | 197 |
| COOH | H | 1 | 1 | 3,5-difluoro | 2-CH$_3$ | H | 198 |
| COOH | CH$_3$ | 1 | 1 | 4-F | 2-CH$_3$ | H | 199 |
| COOH | H | 1 | 1 | 4-F | 3-CH$_3$ | H | 201 |
| COOH | H | 1 | 1 | 4-F | 2-OPFB[2] | H | 202 |
| COOH | H | 1 | 1 | 4-F | 2-F | H | 204 |
| COOH | H | 1 | 1 | 4-F | 2-F | H | 206 |
| OC(CH$_3$)$_2$COOH | H | 1 | 1 | 4-F | 2-CH$_3$ | H | 208 |

[1]OPMB represents —O-para-methoxybenzyl;
[2]OPFB represents —O-para-fluorobenzyl.

TABLE 5

Cellular Luciferase Activity

| Compound No. | Fold[a] (5 µM) | Fold[a] (50 µM) | α EC$_{50}$[b] | γ EC$_{50}$[b] | δ EC$_{50}$[b] |
|---|---|---|---|---|---|
| 91, (10) | 11 | 36 | 5.6 | >100 | >100 |
| 92, (26) | 8 | 21 | 5.1 | >100 | >100 |
| 110 | 1 | 1 | | | |
| 114, (22) | 1 | 59 | 25.3 | 38.6 | 18.3 |
| 115, (28) | 1 | 41 | 2.1 | 8.9 | 5.6 |
| 116, (21) | 1 | 46 | | | |
| 117, (9) | 18 | 35 | | | |
| 118, (13) | 1 | 37 | | | |
| 119, (14) | 9 | 35 | | | |
| 120, (11) | 16 | 35 | | | |
| 121, (24) | 16 | 42 | | | |
| 122, (12) | 17 | 36 | | | |
| 123, (23) | 2 | 55 | | | |
| 125 | 82 | 97 | 0.8 | >100 | >100 |
| 126 | 81 | 100 | 0.8 | | |
| 127 | 11 | 150 | | | |
| 128 | 19 | 106 | | | |
| 129 | 2 | 112 | | | |
| 130 | 2 | 43 | 29.2 | | |
| 133 | 1 | 0 | | | |
| 134 | 3 | 9 | | | |
| 145 | 3 | 5 | | | |
| 146 | 34 | 53 | | | |
| 147 | 3 | 3 | | | |
| 148 | 73 | 85 | 5.7 | | |
| 151 | 102 | 109 | 1.0 | | |
| 153 | 94 | 120 | 1.7 | | |
| 154 | 3 | 2 | | | |
| 158 | 100 | 140 | 1.3 | | |
| 159 | 45 | 121 | | | |
| 168 | 18 | 93 | | | |
| 174 | 2 | 25 | | | |
| 184 | 59 | 69 | 0.9 | | |
| 185 | 61 | 66 | 0.7 | >100 | >100 |
| 187 | 1 | 0 | | | |
| 188 | 10 | 45 | | | |
| 189 | 39 | 37 | 1.2 | | |
| 190 | 69 | 44 | 0.03 | >100 | >100 |
| 191 | 42 | 61 | | | |
| 192 | 53 | 58 | 0.8 | | |
| 193 | 73 | 56 | 1.1 | | |
| 194 | 51 | 49 | 0.4 | >100 | >100 |
| 195 | 34 | 45 | | | |
| 196 | 74 | 72 | | | |
| 197 | 69 | 70 | | | |
| 198 | 88 | 84 | | | |
| 199 | 102 | 131 | | | |
| 201 | 56 | 81 | | | |
| 202 | 74 | 63 | | | |
| 204 | 92 | 102 | | | |
| 206 | 97 | 64 | | | |
| 208 | 78 | 66 | | | |

[a]Fold = fold increase in luciferase compared to DMSO negative control. These values cannot necessarily be used to compare two compounds, as runs may not have occurred under the same conditions.
[b]EC$_{50}$ = compound concentration (µM) that produces 50% maximal activity.

Structure IIb

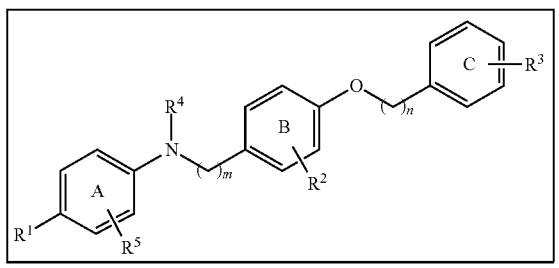

TABLE 6

Representative Examples of Compounds having Chemical Structure IIb

| R¹ | R⁴ | m | n | R³ | R² | R⁵ | Compound No. |
|---|---|---|---|---|---|---|---|
| COOH | H | 1 | 1 | 4-CF₃ | H | H | 155 |
| COOH | H | 1 | 1 | 4-OCH₃ | H | H | 162 |
| OC(CH₃)₂COOH | H | 1 | 1 | 4-F | H | H | 182 |
| COOH | H | 1 | 1 | 4-F | H | H | 183 |

TABLE 7

Cellular Luciferase Activity

| Compound No. | Fold[a] (5 μM) | Fold[a] (50 μM) |
|---|---|---|
| 155 | 4 | 8 |
| 162 | 4 | 29 |
| 182 | 40 | 74 |
| 183 | 4 | 14 |

[a]Fold = fold increase in luciferase compared to DMSO negative control. These values cannot necessarily be used to compare two compounds, as runs may not have occurred under the same conditions.

Figure 4:
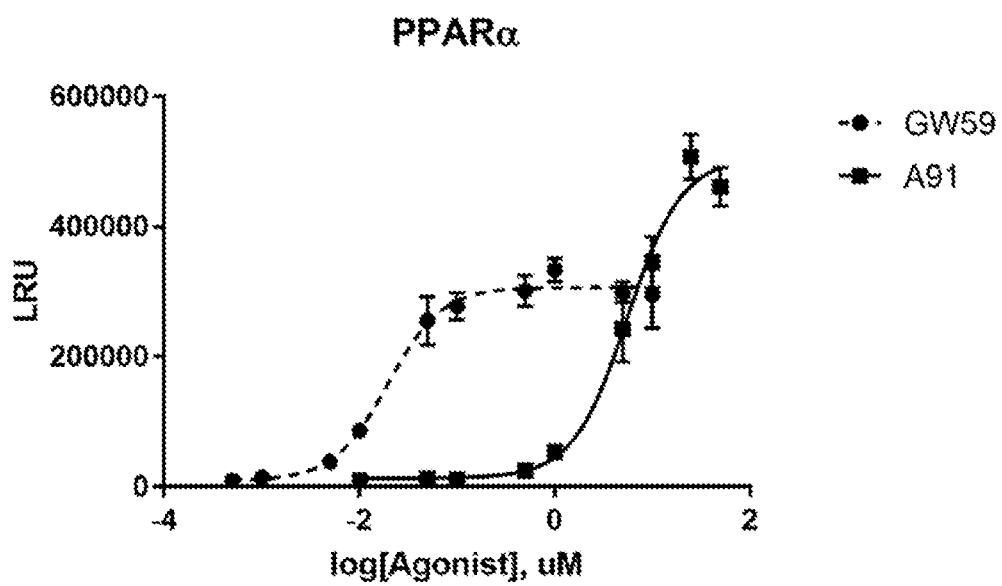
FIG. 4 shows dose-dependent agonism of PPARα by A91 as demonstrated by luciferase quantification (luminescence) in a cell-based luciferase reporter assay. GW 59=GW590735 employed as a positive control. (A91=ASD91=10).
Figure 5:
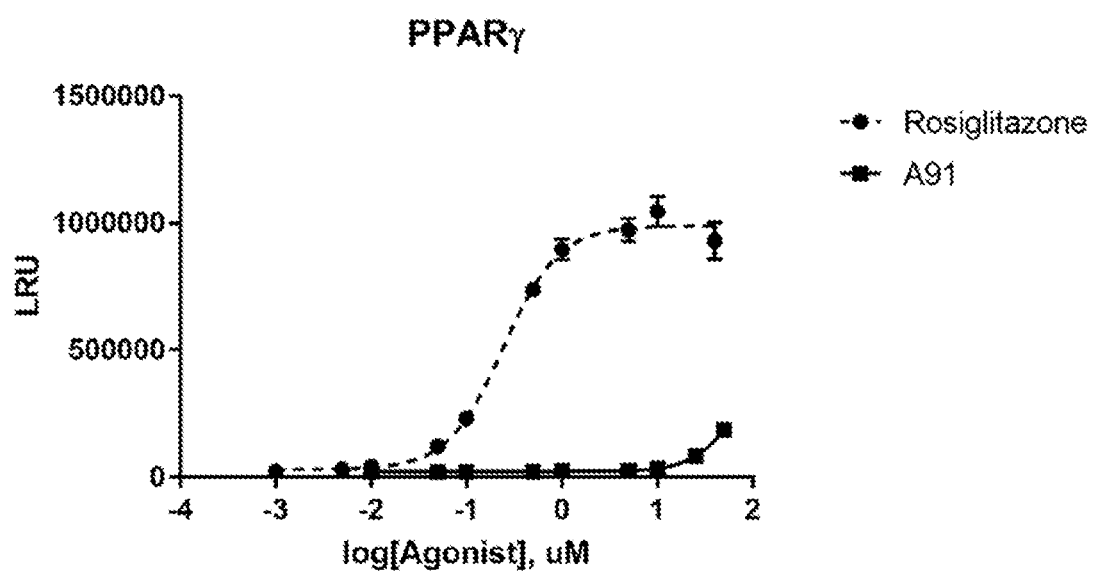
FIG. 5 shows dose-dependent agonism of PPARγ by A91 as demonstrated by luciferase quantification (luminescence) in a cell-based luciferase reporter assay. Rosiglitazone employed as a positive control. (A91=ASD91=10).
Figure 6:
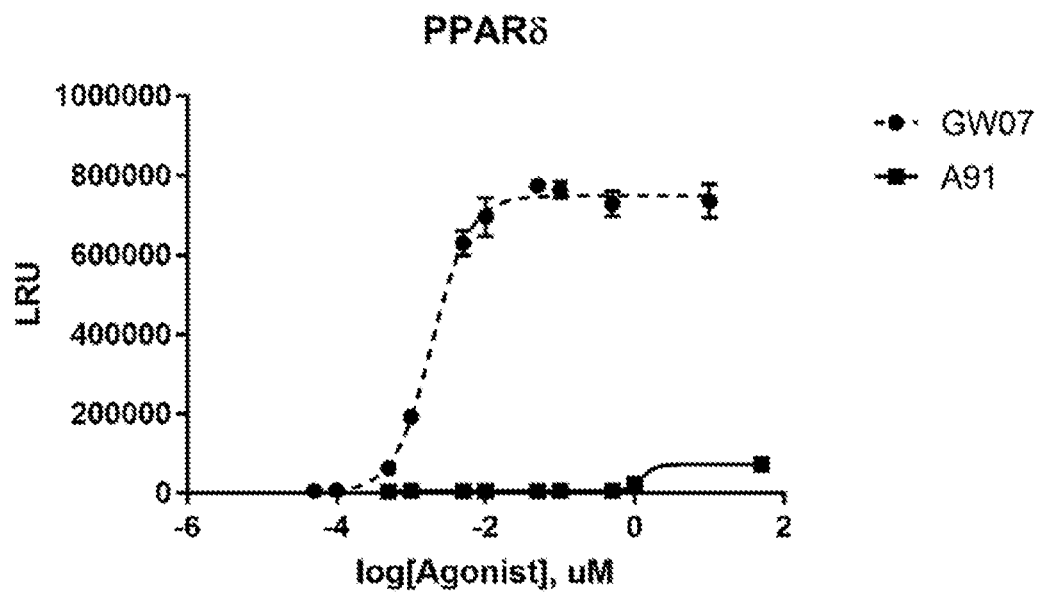
FIG. 6 shows dose-dependent agonism of PPARδ by A91 as demonstrated by luciferase quantification (luminescence) in a cell-based luciferase reporter assay. GW 07=GW0742 employed as a positive control. (A91=ASD91=10).
Figure 7:
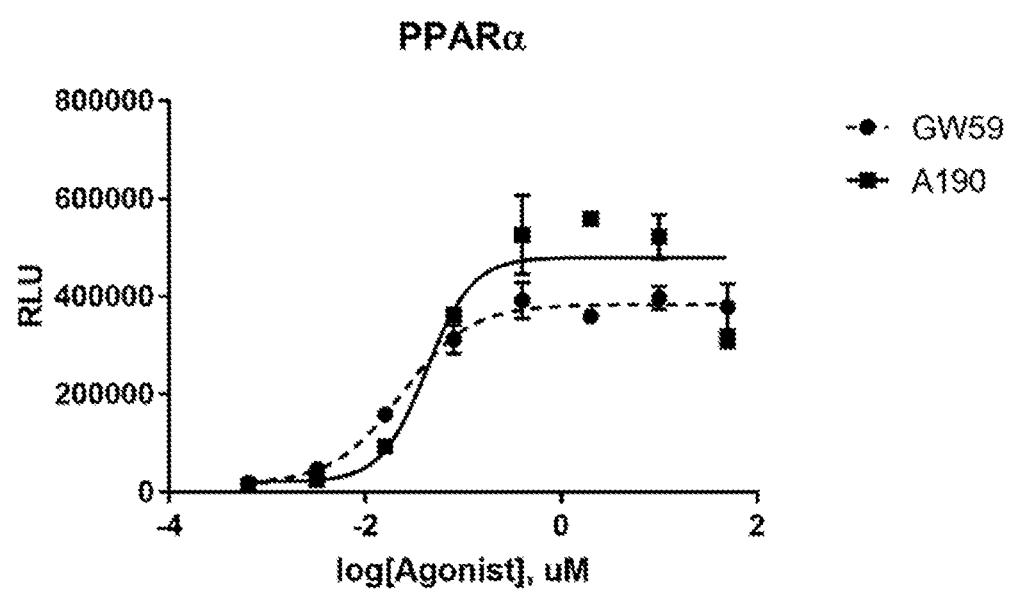
FIG. 7 shows dose-dependent agonism of PPARα by A190 as demonstrated by luciferase quantification (luminescence) in a cell-based luciferase reporter assay. GW 59=GW590735 employed as a positive control. (A190=190=ASD190).
Figure 8:
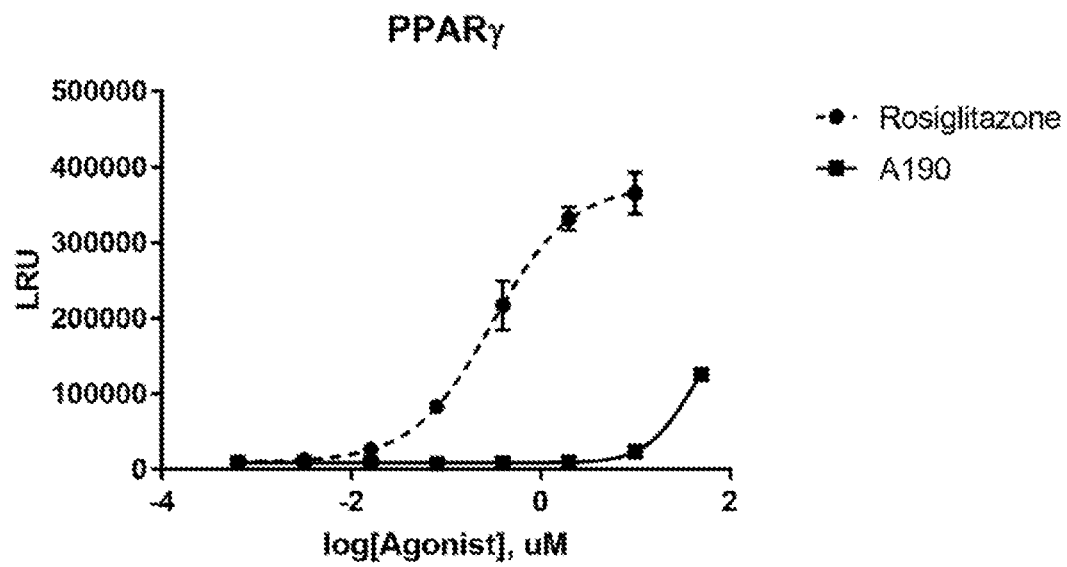
FIG. 8 shows dose-dependent agonism of PPARγ by A190 as demonstrated by luciferase quantification (luminescence) in a cell-based luciferase reporter assay. Rosiglitazone employed as a positive control. (A190=190=ASD190).
Figure 9:
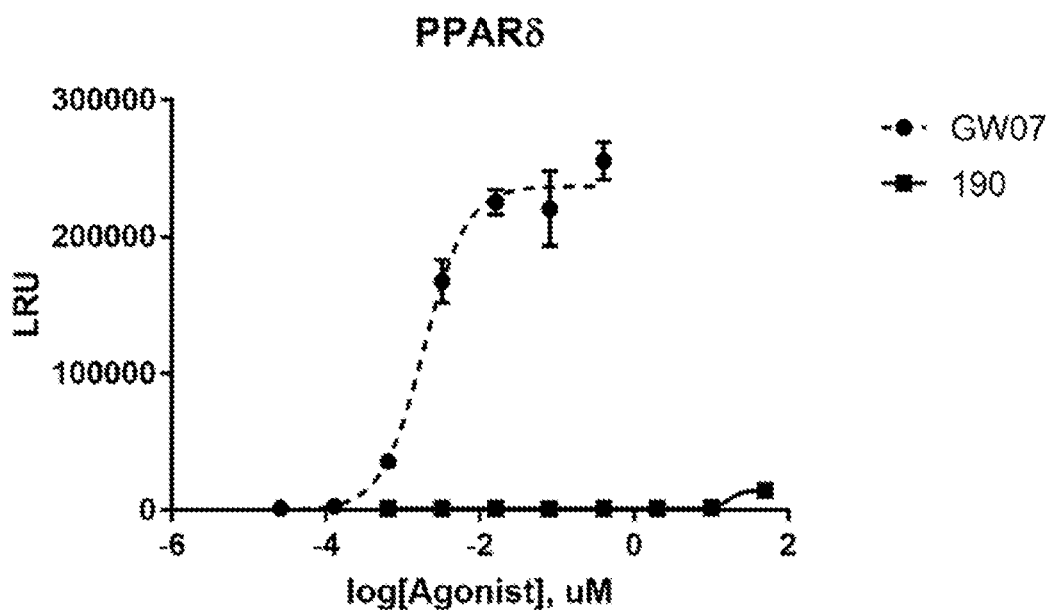
FIG. 9 shows dose-dependent agonism of PPARδ by A190 as demonstrated by luciferase quantification (luminescence) in a cell-based luciferase reporter assay. GW 07=GW0742 employed as a positive control. (A190=190=ASD190).

The data in Tables 4-7 demonstrate that this chemotype is active in a whole-cell setting and engages the desired target, PPARα. Additionally, the results demonstrate definitive structure-activity relationships, a tunable level of agonism, and the selectivity profile of this chemotype for PPARα over the other isoforms. The results shown in FIGS. 4-6 demonstrate that compound 91 (10) exhibits dose-dependent activity in a cell-based activity and exhibits >20-fold selectivity over other isoforms. The results shown in FIGS. 7-9 demonstrate that compound 190 exhibits dose-dependent activity in a cell-based activity and exhibits >2000-fold selectivity over other isoforms. This demonstrates that potency of this chemotype can be improved while enhancing or maintaining selectivity.

Figure 10A:
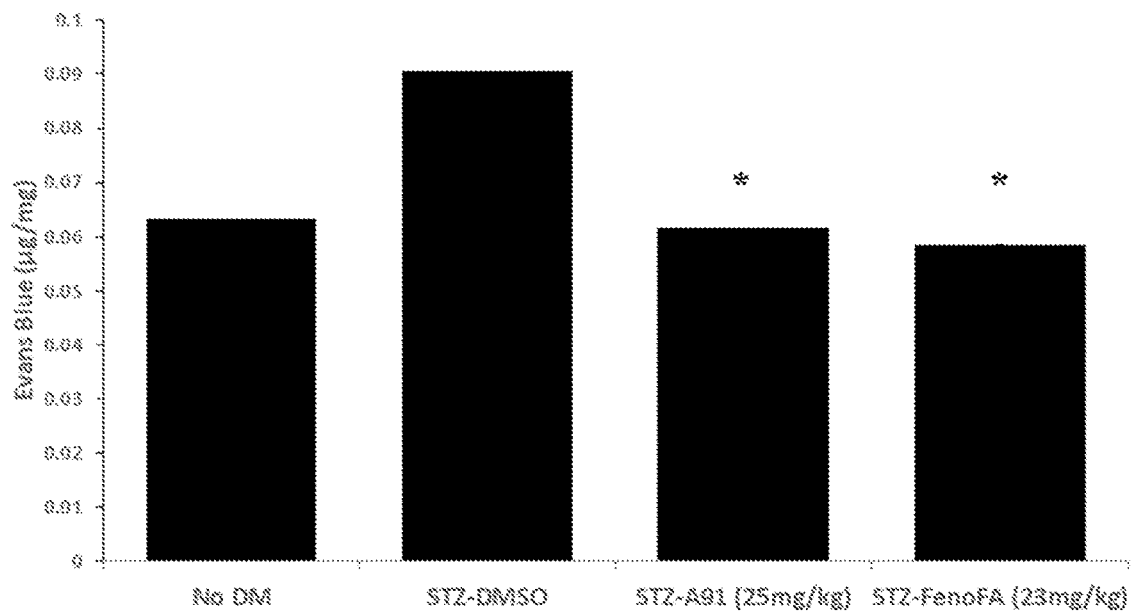
FIG. 10A shows results of the in vivo efficacy of Compound ASD91(10) on retinal permeability in comparison to fenofibric acid (FenoFA). 7-8 week-old male Brown Norway rats were injected with streptozotocin (STZ, 55 mg/kg). Two weeks after STZ injections, daily treatment (i.p. injection) with ASD091 or FenoFA commenced and lasted for 26-28 days. ≠$P<0.05$ (vs. FenoFA), *$P<0.05$ (vs. STZ-DMSO).
Figure 10B:
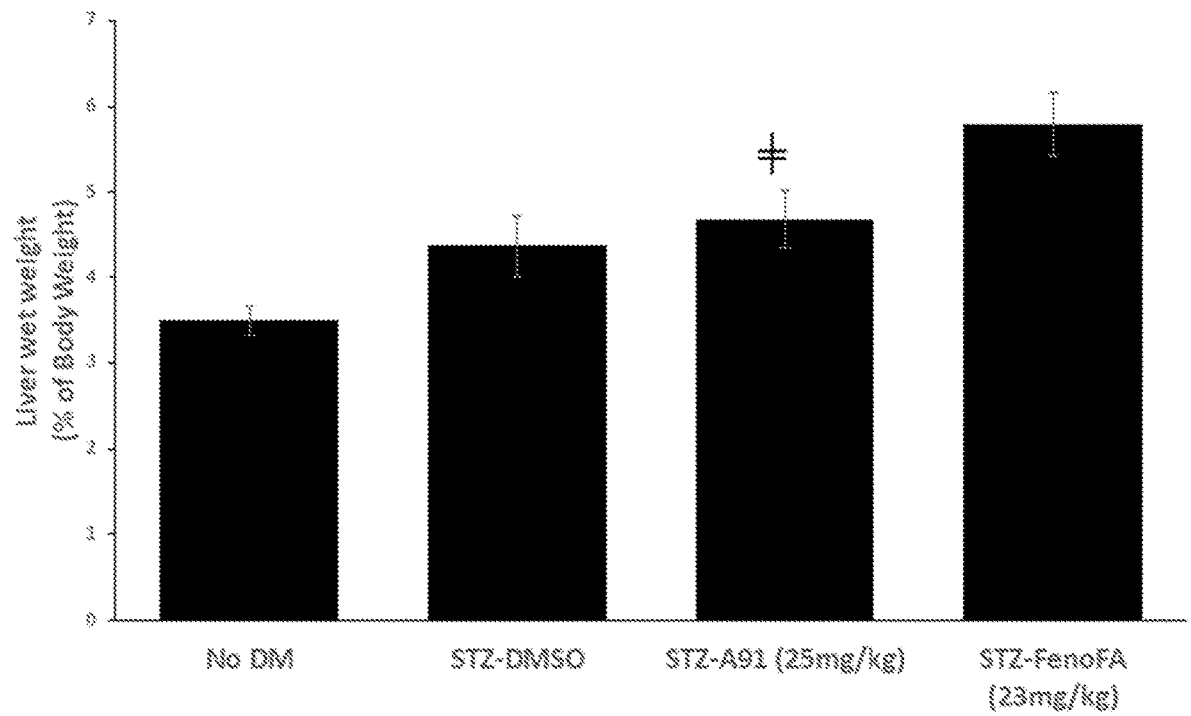
FIG. 10B shows results of the in vivo efficacy of Compound ASD91(10) on liver phenotype in comparison to fenofibric acid (FenoFA). 7-8 week-old male Brown Norway rats were injected with streptozotocin (STZ, 55 mg/kg). Two weeks after STZ injections, daily treatment (i.p. injection) with ASD091 or FenoFA commenced and lasted for 26-28 days. ≠$P<0.05$ (vs. FenoFA), *$P<0.05$ (vs. STZ-DMSO).

The data in FIGS. 10A and 10B show that pharmacological activation of PPARα in humans has clinical benefits on reducing the prevalence of diabetic retinopathy, as reported in FIELD and ACCORD studies. We demonstrate in FIGS. 10A and 10B that compound 91 exhibits in vivo efficacy in a well-established STZ-rat model of diabetic retinopathy (DR). As shown in FIGS. 10A and 10B, compound 91 reduces retinal vascular leakage in diabetic rats—a major culprit behind diabetic macular edema and consequential vision loss. Of interesting note, compound 91 seems to lack signs of hepatomegaly, a common side-effect of fenofibrate that may impose dose-limiting toxicity. These initial results provide proof-of-concept that compound 91 (1) demonstrates in vivo efficacy in a relevant DR model following systemic administration, (2) crosses blood-ocular barrier and reaches the retina, (3) is bioavailable, (4) survives first-pass metabolism and clearance mechanisms well enough to maintain efficacy, and (5) demonstrates a relatively safe profile (no observable toxicity) after daily injection for one-month.

These studies demonstrate therapeutic use of ophthalmic compositions comprising this new class of compounds for the treatment of ocular disorders and conditions such as but not limited to retinal inflammation, retinal neovascularization, retinal vascular leakage, retinopathy of prematurity, diabetic retinopathy, age-related macular degeneration, and diabetic macular edema, and other ocular and non-ocular diseases and/or conditions described herein.

While the present disclosure has been described herein in connection with certain embodiments so that aspects thereof may be more fully understood and appreciated, it is not intended that the present disclosure be limited to these particular embodiments. On the contrary, it is intended that all alternatives, modifications and equivalents are included within the scope of the present disclosure as defined herein. Thus the examples described above, which include particular embodiments, will serve to illustrate the practice of the inventive concepts of the present disclosure, it being understood that the particulars shown are by way of example and for purposes of illustrative discussion of particular embodiments only and are presented in the cause of providing what is believed to be the most useful and readily understood description of procedures as well as of the principles and conceptual aspects of the present disclosure. Changes may be made in the formulation of the various compositions described herein, the methods described herein or in the steps or the sequence of steps of the methods described herein without departing from the spirit and scope of the present disclosure. Further, while various embodiments of the present disclosure have been described in claims herein below, it is not intended that the present disclosure be limited to these particular claims.

What is claimed is:

1. A compound, comprising chemical structure II:

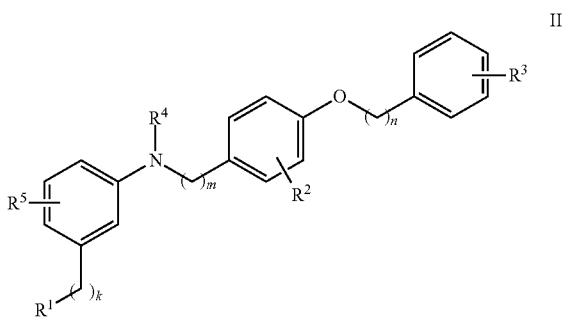

wherein:
k is 0;
m is 1;
n is 1;
R¹ is selected from the group consisting of COOH, OC(CH₃)₂COOH, B(OH)₂, OCH₂COOH, NHSO₂CH₃, SO₂NH₂, tetrazole, SC(CH₃)₂COOH, and salts thereof;
R² is selected from the group consisting of hydrogen (H), CH₃, OCH₃, F, difluoro, Br, dibromo, Cl, dichloro, I, diiodo, $CF_3$, $CBr_3$, $CCl_3$, $CI_3$, O-para-methoxybenzyl, and O-para-fluorobenzyl;

$R^3$ is selected from the group consisting of H, F, difluoro, Br, dibromo, Cl, dichloro, I, diiodo, $CF_3$, $CBr_3$, $CCl_3$, $CI_3$, $NO_2$, CN, $CH_3$, $OCH_3$, O-para-methoxybenzyl, and O-para-fluorobenzyl;

$R^4$ is H or $CH_3$;

$R^5$ is selected from the group consisting of H, F, Br, Cl, I, and $CH_3$; and wherein the compound has PPARα agonistic activity, and with the proviso that when $R^1$=COOH, at least one of $R^2$-$R^5$ is not H;

when $R^1$=COOH and $R^3$=$CH_3$, at least one of $R^2$, $R^4$, and $R^5$ is not H; and when $R^2$-$R^5$=H, $R^1$ is not tetrazole.

2. A composition, comprising one or more compounds of claim 1 disposed in a pharmaceutically-acceptable carrier, vehicle, or diluent.

3. The composition of claim 2, formulated to provide a delayed release, controlled release, extended release, and/or sustained release of the one or more compounds.

4. A kit, comprising the composition of claim 2, and instructions for use thereof in a treatment of a disorder or condition in a subject.

5. The kit of claim 4, wherein the disorder or condition is an ocular disorder or condition selected from the group consisting of retinal inflammation, retinal neovascularization, retinal vascular leakage, retinopathy of prematurity (ROP), diabetic retinopathy (DR), an age-related macular degeneration (AMD), macular edema, diabetic macular edema (DME), keratitis, endophthalmitis, blepharitis, conjunctivitis, scleritis, herpetic inflammation, uveitis, vasculitis, arteritis, orbital inflammations, optic neuritis, sympathetic ophthalmia, retinitis, glaucoma, proliferative vitreoretinopathy, corneal edema, uveal edema, and retinal edema.

6. A method of increasing peroxisome proliferator-activated receptor α (PPARα) activity in a retinal cell, comprising: administering to the retinal cell a PPARα activity-enhancing amount of a compound comprising chemical structure II:

II wherein:
k is 0;
m is 1;
n is 1;
$R^1$ is selected from the group consisting of COOH, $OC(CH_3)_2COOH$, $B(OH)_2$, $OCH_2COOH$, $NHSO_2CH_3$, $SO_2NH_2$, tetrazole, $SC(CH_3)_2COOH$, and salts thereof;
$R^2$ is selected from the group consisting of hydrogen (H), $CH_3$, $OCH_3$, F, difluoro, Br, dibromo, Cl, dichloro, I, diiodo, $CF_3$, $CBr_3$, $CCl_3$, $CI_3$, O-para-methoxybenzyl, and O-para-fluorobenzyl;

$R^3$ is selected from the group consisting of H, F, difluoro, Br, dibromo, Cl, dichloro, I, diiodo, $CF_3$, $CBr_3$, $CCl_3$, $CI_3$, $NO_2$, CN, $CH_3$, $OCH_3$, O-para-methoxybenzyl, and O-para-fluorobenzyl;

$R^4$ is H or $CH_3$;

$R^5$ is selected from the group consisting of H, F, Br, Cl, I, and $CH_3$; and wherein the compound has PPARα agonistic activity.

7. A method of treating a disorder or condition in a subject by causing an increase in peroxisome proliferator-activated receptor α (PPARα) activity, comprising: administering to a subject in need of such therapy, a therapeutic amount of a compound comprising chemical structure II:

II wherein:
k is 0;
m is 1;
n is 1;
$R^1$ is selected from the group consisting of COOH, $OC(CH_3)_2COOH$, $B(OH)_2$, $OCH_2COOH$, $NHSO_2CH_3$, $SO_2NH_2$, tetrazole, $SC(CH_3)_2COOH$, and salts thereof;
$R^2$ is selected from the group consisting of hydrogen (H), $CH_3$, $OCH_3$, F, difluoro, Br, dibromo, Cl, dichloro, I, diiodo, $CF_3$, $CBr_3$, $CCl_3$, $CI_3$, O-para-methoxybenzyl, and O-para-fluorobenzyl;

$R^3$ is selected from the group consisting of H, F, difluoro, Br, dibromo, Cl, dichloro, I, diiodo, $CF_3$, $CBr_3$, $CCl_3$, $CI_3$, $NO_2$, CN, $CH_3$, $OCH_3$, O-para-methoxybenzyl, and O-para-fluorobenzyl;

$R^4$ is H or $CH_3$;

$R^5$ is selected from the group consisting of H, F, Br, Cl, I, and $CH_3$; and wherein the compound has PPARα agonistic activity.

8. The method of claim 7, wherein the disorder or condition is selected from the group consisting of retinal inflammation, retinal neovascularization, retinal vascular leakage, retinopathy of prematurity (ROP), diabetic retinopathy (DR), an age-related macular degeneration (AMD), and diabetic macular edema (DME).

9. The method of claim 7, wherein the disorder or condition is characterized by inflammation and/or angiogenesis.

10. The method of claim 7, wherein the disorder is selected from inflammatory bowel disease, type 1 diabetes, type 2 diabetes, Graves disease, multiple sclerosis, osteoarthritis, rheumatoid arthritis, vasculitis, dermatitis, glomerulonephritis, hepatitis, periodonititis, atherosclerosis, heart failure, obesity, Alzheimer's disease, and metabolic syndrome.

11. The method of claim 7, wherein the disorder or condition is an ocular disorder or condition selected from keratitis, endophthalmitis, blepharitis, conjunctivitis, scleritis, herpetic inflammation, uveitis, vasculitis, arteritis, orbital inflammations, optic neuritis, sympathetic ophthalmia, retinitis, macular edema, glaucoma, proliferative vitreoretinopathy, corneal edema, uveal edema, and retinal edema.

12. The method of claim 7, wherein the disorder or condition is selected from retinal artery or vein occlusion, corneal graft rejection, corneal neovascularization, neovascular glaucoma, sickle cell retinopathy, cancers, skin diseases, diabetic ulcers, diabetic nephropathy, cardiovascular disease, and stroke.

13. The method of claim 7, wherein the compound is provided in a composition formulated to provide a delayed release, controlled release, extended release, and/or sustained release of the compound.

* * * * *